US011682486B1

(12) United States Patent
Myers et al.

(10) Patent No.: US 11,682,486 B1
(45) Date of Patent: Jun. 20, 2023

(54) METHOD, APPARATUS AND COMPUTER PROGRAM PRODUCT FOR A CLINICAL RESOURCE MANAGEMENT SYSTEM

(71) Applicant: LHC Group, Inc., Lafayette, LA (US)

(72) Inventors: Keith G. Myers, Sunset, LA (US); Raj Shetye, Lafayette, LA (US)

(73) Assignee: LHC Group, Inc., Lafayette, LA (US)

( * ) Notice: Subject to any disclaimer, the term of this patent is extended or adjusted under 35 U.S.C. 154(b) by 310 days.

(21) Appl. No.: 16/735,796

(22) Filed: Jan. 7, 2020

(51) Int. Cl.
| | |
|---|---|
| *G16H 40/20* | (2018.01) |
| *G06N 20/00* | (2019.01) |
| *G06Q 10/0639* | (2023.01) |
| *G16H 10/60* | (2018.01) |
| *G16H 70/20* | (2018.01) |
| *G06N 7/01* | (2023.01) |

(52) U.S. Cl.
CPC .............. *G16H 40/20* (2018.01); *G06N 7/01* (2023.01); *G06N 20/00* (2019.01); *G06Q 10/06398* (2013.01); *G16H 10/60* (2018.01); *G16H 70/20* (2018.01)

(58) Field of Classification Search
CPC ......... G16H 40/20; G06N 7/005; G06N 20/00; G06Q 10/06398; G16H 10/60; G16H 70/20
See application file for complete search history.

(56) References Cited

U.S. PATENT DOCUMENTS

| | | | |
|---|---|---|---|
| 7,505,916 B1 | 3/2009 | Adrian et al. | |
| 7,844,473 B1 | 11/2010 | Adrian et al. | |
| 2010/0274580 A1* | 10/2010 | Crownover et al. | G06Q 10/06 705/2 |
| 2018/0293502 A1* | 10/2018 | Sengupta | G06N 5/022 |
| 2020/0034772 A1* | 1/2020 | Balan | G06Q 40/125 |
| 2021/0350910 A1* | 11/2021 | Dastmalchi et al. | G06Q 10/1097 |

FOREIGN PATENT DOCUMENTS

| | | | | |
|---|---|---|---|---|
| GB | 2392748 A | * | 3/2004 | G066Q 40/02 |
| WO | 2020006495 A1 | * | 1/2020 | G06F 40/205 |

OTHER PUBLICATIONS

Grimaldi, Medicare's new home health prospective payment system explained, Nov. 2000, Healthcare Financial Management, pages 46-56. (Year: 2000).*
Swallow et al., United States: Home Health Prospective Payment System Update And Redesign: Part Deux?, Jul. 16, 2018, Mondaq.com. (Year: 2018).*
Vontran et al., Overview of the Patient-Driven Groupings Model (PDGM), Feb. 12, 2019, Medicare Learning Network, pages 1-82. (Year: 2019).*
Ma et al., Incorporating medical code descriptions for diagnosis prediction in healthcare, Dec. 2018, BMC Medical Informatics and Decision Making, pages 1-13. (Year: 2018).*

* cited by examiner

*Primary Examiner* — Christopher L Gilligan
(74) *Attorney, Agent, or Firm* — Alston & Bird LLP

(57) ABSTRACT

Methods, apparatus, systems, computing devices, computing entities, and/or the like for a clinical resource management system are provided. An example clinical resource management system may determine a first model service value point associated with a first time period and a second model service value point associated with a second time period, calculate a first projected service value point and a second projected service value point, and calculate an aggregated service value point balance.

19 Claims, 14 Drawing Sheets

| Smallville | Adjustment Type | | Visit Type | | | | | | | |
|---|---|---|---|---|---|---|---|---|---|---|
| | All | | Actual ◎ Model ○ SVP | | | | | | Actual Visit Count | |
| Patient | Start | End | % | Available | Used | Balance | HHRG | Adjustment | RN | LPN |
| Aaron, John | 06/18/2019 | 08/16/2019 | -38% | 38 | 49 | -13 | C3F3S2 | No Adjustment | 8 | 2 |
| Butler, Jose | 06/25/2019 | 08/23/2019 | 6% | 18 | 17 | 1 | C2F3S1 | No Adjustment | 2 | 6 |
| Brown, Amy | 06/27/2019 | 08/25/2019 | 0% | 0 | 0 | 0 | | LUPA | 2 | 7 |
| Edwards, Sam | 06/16/2019 | 08/14/2019 | 0% | 62 | 62 | 0 | C3F3S5 | Positive Adjustment 3 | | 14 |
| Evans, Arthur | 06/12/2019 | 08/10/2019 | 0% | 0 | 0 | 0 | | Outliner | 3 | 5 |
| Garcia, Tim | 07/17/2019 | 09/14/2019 | -2% | 58 | 59 | -1 | C1F3S5 | No Adjustment | 0 | 8 |
| Gonzalez, Bill | 06/13/2019 | 08/11/2019 | 15% | 18 | 15 | -3 | C2F3S1 | No Adjustment | 10 | 0 |
| Lopez Michael | 07/19/2019 | 09/16/2019 | -7% | 22 | 23 | -1 | C3F3S1 | No Adjustment | 1 | 6 |
| Moore, Chris | 06/19/2019 | 08/17/2019 | 19% | 18 | 14 | 3 | C2F3S1 | No Adjustment | 1 | 3 |
| Roberts, Melissa | 06/14/2019 | 08/12/2019 | 66% | 20 | 7 | 14 | C1F3S1 | No Adjustment | 4 | 3 |
| Roger, George | 07/10/2019 | 09/07/2019 | 23% | 22 | 17 | 5 | C3F3S1 | No Adjustment | 2 | 3 |
| Wilson, Stephen | 07/12/2019 | 09/09/2019 | 47% | 23 | 12 | 11 | C3F3S1 | No Adjustment | 0 | 4 |
| Wright, Laura | 07/03/2019 | 08/31/2019 | 66% | 18 | 6 | 12 | C2F3S1 | No Adjustment | 0 | 6 |
| Zabel, Dan | 07/20/2019 | 09/17/2019 | 47% | 52 | 28 | 25 | C3F3S4 | Positive Adjustment 1 | | 8 |

Fig. 13

METHOD, APPARATUS AND COMPUTER PROGRAM PRODUCT FOR A CLINICAL RESOURCE MANAGEMENT SYSTEM

TECHNOLOGICAL FIELD

Embodiments of the present disclosure generally relate to a clinical resource management system. More specifically, various embodiments of the present disclosure may programmatically evaluate and/or improve clinical resource efficiency for healthcare providers.

BACKGROUND

Healthcare providers face challenges in managing clinical resources. For example, after a patient moves from an acute care setting (for example, receive care in a hospital emergency department) to a post-acute care setting (for example, receive care at home), a healthcare provider may need to evaluate the condition of the patient and determine whether additional visits to the patient residence may be necessary. If additional visits are necessary, the healthcare provider may also need to determine the type of healthcare professional (e.g. home health aide, certified nursing assistant, licensed practical nurse, registered nurse) to visit the patient and the amount or frequency of such visit(s). However, clinical resource of a healthcare provider may be limited, and it can be challenging to achieve a balance between providing quality healthcare service and maintaining the efficient utilization of clinical resources.

In addition, regulatory changes may affect clinical resource management. For example, the Centers for Medicare and Medicaid Services (CMS) previously required home health agencies to complete an outcome and assessment information set (OASIS) on each patient for a 60-day unit of payment (also known as an "episode"). The result of the assessment may group each episode into one of 153 home health resource groups (HHRGs) based on clinical levels, functional levels, and service use categories. In 2019, the CMS finalized rules reflecting significant changes to the HHRG. The new model, Patient-Driven Groupings Model (PDGM), has a 30-day episode instead of a 60-day episode, and each 30-day episode is placed into one of 432 HHRGs based on admission source, timing, clinical grouping, functional impairment level, and comorbidity adjustment. As such, methods previously employed by healthcare providers (especially home health agencies) for allocating clinical resource and projecting costs and reimbursements may be rendered obsolete by the changes to HHRG.

BRIEF SUMMARY

In general, embodiments of the present disclosure provide methods, apparatus, systems, computing devices, computing entities, and/or the like.

In accordance with one aspect, an apparatus for programmatically evaluating clinical resource efficiency may be provided. The apparatus may comprise at least one processor and at least one non-transitory memory comprising program code. The at least one non-transitory memory and the program code may be configured to, with the at least one processor, cause the apparatus to at least: determine a first model service value point and a second model service value point for a patient profile, wherein the first model service value point is associated with a first time period and the second model service value point is associated with a second time period; retrieve one or more weight values associated with one or more types of healthcare professional visits from a home healthcare provider for the patient profile; determine a first plurality of projected visit numbers associated with the first time period and a second plurality of projected visit numbers associated with the second time period; determine at least one machine learning model based on the patient profile for calculating projected service value points; calculate a first projected service value point based at least in part on the one or more weight values, the first plurality of projected visit numbers, and the at least one machine learning model; calculate a second projected service value point based at least in part on the one or more weight values, the second plurality of projected visit numbers, and the at least one machine learning model; and calculate an aggregated service value point balance based at least in part on the first model service value point, the first projected service value point, the second model service value point, and the second projected service value point.

In accordance with another aspect, the at least one non-transitory memory and the program code are configured to, with the at least one processor, cause the apparatus to further: cause a display of a clinical resource management interface. In some examples, the clinical resource management interface may comprise a first window portion and a second window portion. In some examples, the first window portion may indicate the first model service value point and the first projected service value point. In some examples, the second window portion may indicate the second model service value point and the second projected service value point.

In accordance with another aspect, when determining the model service value point for the first patient episode, the at least one non-transitory memory and the program code may be configured to, with the at least one processor, cause the apparatus to further: retrieve visit distribution pattern data associated with the home healthcare provider; determine, based on the visit distribution pattern data, one or more model visit numbers corresponding to the one or more types of healthcare professional visits associated with a first Home Health Resource Groups (HHRG) code corresponding to the first time period; and calculate the first model service value point associated with the first time period based at least in part on the one or more model visit numbers and the one or more weight values.

In accordance with another aspect, when determining the first model service value point and the second model service value point, the at least one non-transitory memory and the program code are configured to, with the at least one processor, cause the apparatus to further: retrieve patient episode data corresponding to a plurality of patient episodes associated with the home healthcare provider, wherein the patient episode data comprises episode descriptors associated with the plurality of patient episodes; determine, based on the episode descriptors, a plurality of HHRG codes corresponding to the plurality of patient episodes under a Patient-Driven Groupings Model (PDGM); and calculate model service value points for the plurality of HHRG codes under the PDGM based on the patient episode data.

In accordance with another aspect, the at least one non-transitory memory and the program code may be configured to, with the at least one processor, cause the apparatus to further: update the first model service value point associated with the first time period based on actual visit numbers associated with one or more patients having a same HHRG code.

In accordance with another aspect, the at least one non-transitory memory and the program code may be configured to, with the at least one processor, cause the apparatus to further: retrieve patient episode data corresponding to a plurality of patient episodes associated with the home healthcare provider; determining a plurality of model service value points for the plurality of patient episodes; calculating a plurality of projected service value points based on a plurality of projected visit numbers for the plurality of patient episodes and the one or more weight values; and calculating a portfolio service value point balance based at least in part on the plurality of model service value points and the plurality of projected service value points.

In accordance with another aspect, the at least one non-transitory memory and the program code are configured to, with the at least one processor, cause the apparatus to further: determine whether the aggregated service value point balance satisfies a service value point threshold; and in response to determining that the aggregated service value point balance does not satisfy the service value point threshold, generate an alert message.

In accordance with one aspect, a computer-implemented method for programmatically evaluating and/or improving clinical resource efficiency may be provided. The computer-implemented method may comprise determining a first model service value point and a second model service value point for a patient profile, wherein the first model service value point is associated with a first time period and the second model service value point is associated with a second time period; retrieving one or more weight values associated with one or more types of healthcare professional visits from a home healthcare provider for the patient profile; determining a first plurality of projected visit numbers associated with the first time period and a second plurality of projected visit numbers associated with the second time period; determining at least one machine learning model based on the patient profile for calculating projected service value points; calculating a first projected service value point based at least in part on the one or more weight values, the first plurality of projected visit numbers, and the at least one machine learning model; calculating a second projected service value point based at least in part on the one or more weight values, the second plurality of projected visit numbers, and the at least one machine learning model; and calculating an aggregated service value point balance based at least in part on the first model service value point, the first projected service value point, the second model service value point, and the second projected service value point.

In accordance with one aspect, a computer program product may be provided. The computer program product may comprise at least one non-transitory computer-readable storage medium having computer-readable program code portions stored therein. The computer-readable program code portions may comprise an executable portion configured to: determine a first model service value point and a second model service value point for a patient profile, wherein the first model service value point is associated with a first time period and the second model service value point is associated with a second time period; retrieve one or more weight values associated with one or more types of healthcare professional visits from a home healthcare provider for the patient profile; determine a first plurality of projected visit numbers associated with the first time period and a second plurality of projected visit numbers associated with the second time period; determine at least one machine learning model based on the patient profile for calculating projected service value points; calculate a first projected service value point based at least in part on the one or more weight values, the first plurality of projected visit numbers, and the at least one machine learning model; calculate a second projected service value point based at least in part on the one or more weight values, the second plurality of projected visit numbers, and the at least one machine learning model; and calculate an aggregated service value point balance based at least in part on the first model service value point, the first projected service value point, the second model service value point, and the second projected service value point.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 1:
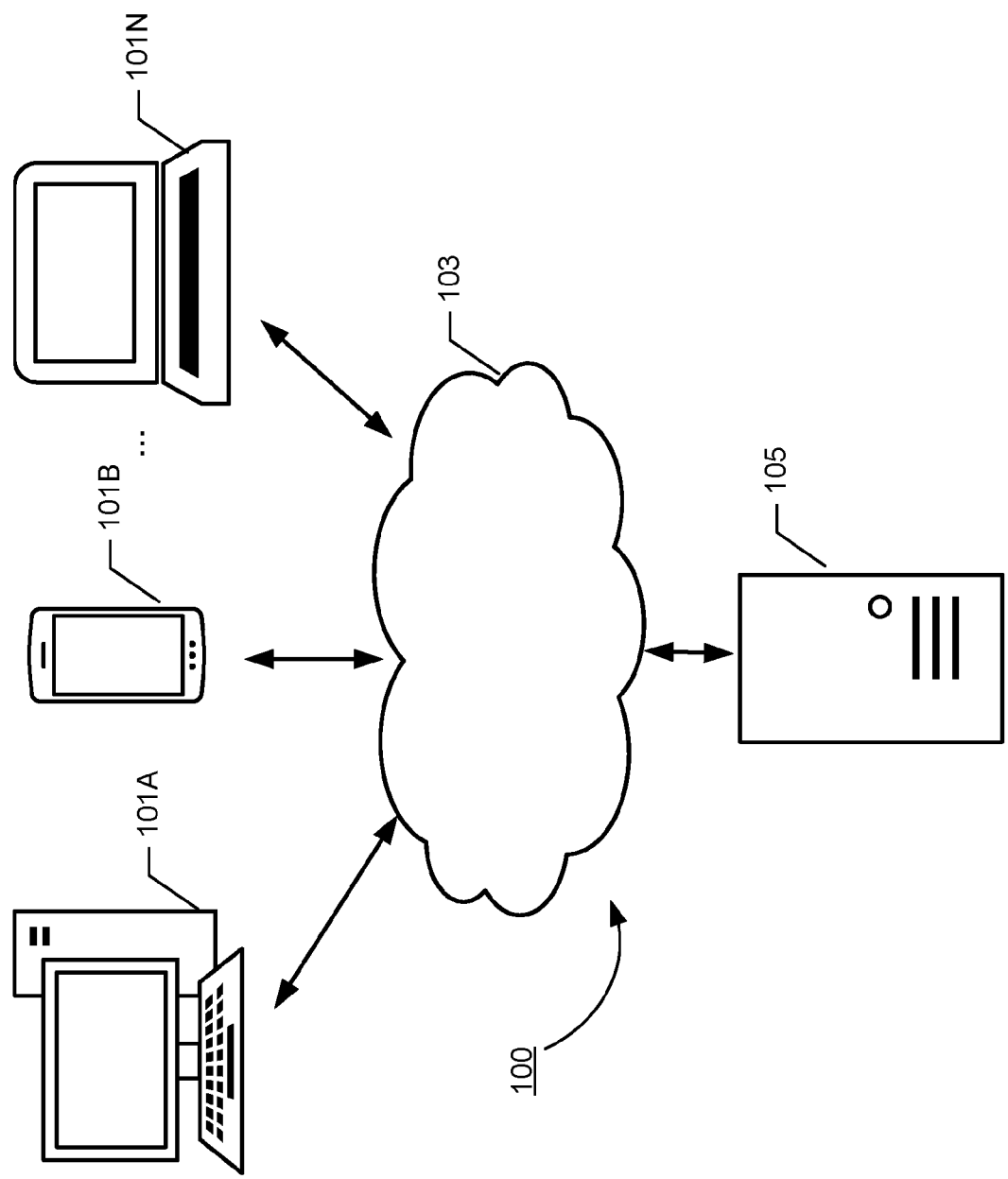
FIG. 1 is a diagram of an example clinical resource management platform/system that can be used in accordance with various embodiments of the present disclosure.

FIGS. 4, 5, 6, 7, 8, and 9 provide example flowcharts illustrating example steps, processes, procedures, and/or operations associated with an example clinical resource management system, in accordance with an example embodiment of the present disclosure; and FIGS. 10, 11, 12, 13, and 14 provide example views of example user interfaces, in accordance with an example embodiment of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily refer to the same embodiment).

I. Computer Program Products, Methods, and Computing Entities

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a clinical resource management platform/system 100 that can be used in conjunction with various embodiments of the present disclosure. As shown in FIG. 1, the clinical resource management platform/system 100 may comprise one or more clinical resource computing entities 105, one or more user computing entities 101A, 101B, ... 101N, and one or more networks 103. Each of the components of the clinical resource management platform/system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

A. Exemplary Clinical Resource Computing Entity

Figure 2:
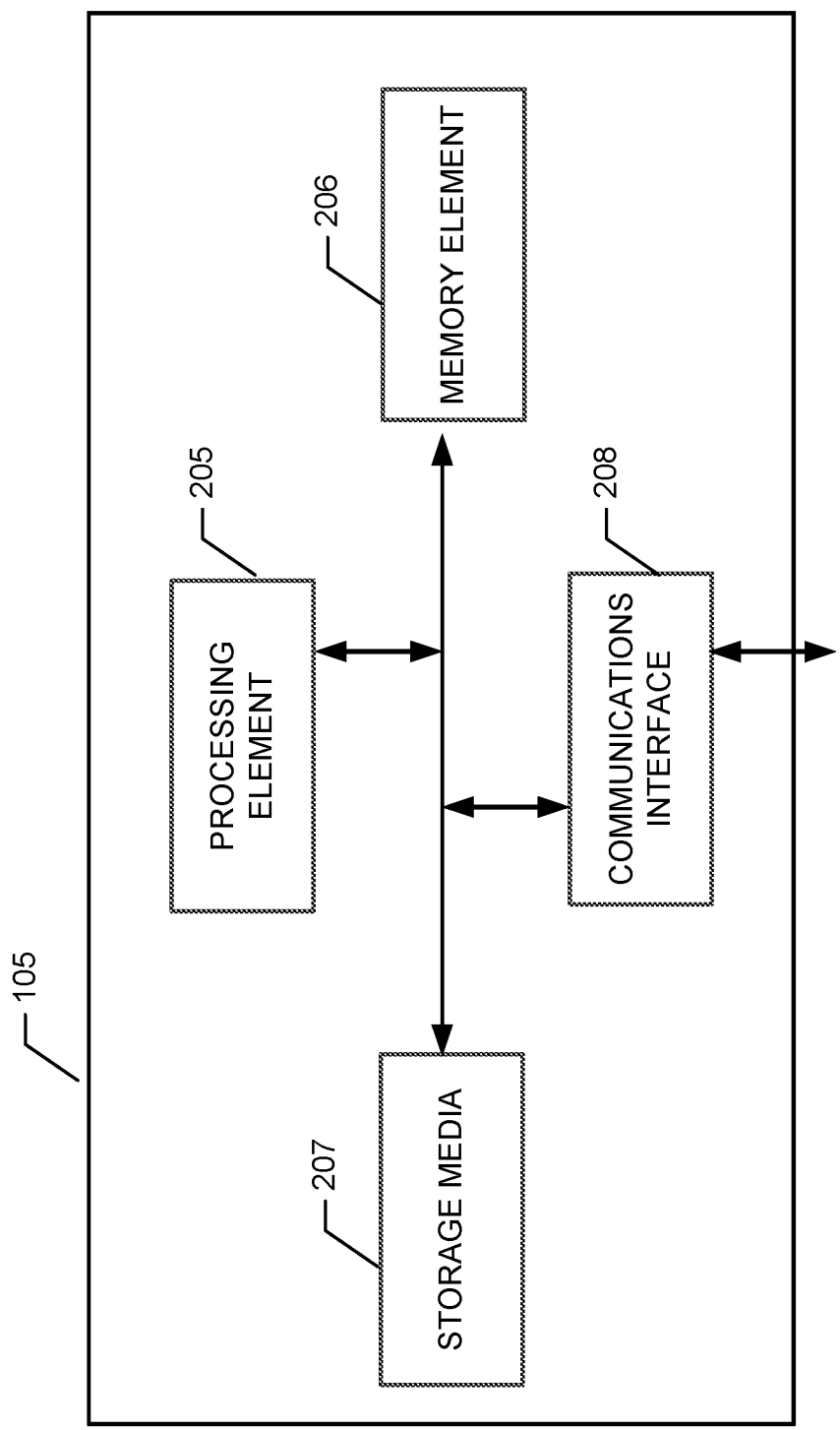
FIG. 2 is a schematic representation of an example clinical resource computing entity in accordance with various embodiments of the present disclosure.

FIG. 2 provides a schematic of a clinical resource computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the clinical resource computing entity 105 may also include one or more network and/or communications interfaces 208 for communicating with various computing entities, such as by communicating data, content, information, and/or similar terms used herein that can be transmitted, received, operated on, processed, displayed, stored, and/or the like. For instance, the clinical resource computing entity 105 may communicate with other clinical resource computing entities 105, one or more user computing entities 101A-101N, and/or the like.

As shown in FIG. 2, in one embodiment, the clinical resource computing entity 105 may include or be in communication with one or more processing elements 205 (also referred to as processors, processing circuitry, and/or similar terms used herein interchangeably) that communicate with other elements within the clinical resource computing entity 105 via a bus, for example, or network connection. As will be understood, the processing element 205 may be embodied in a number of different ways. For example, the processing element 205 may be embodied as one or more complex programmable logic devices (CPLDs), microprocessors, multicore processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the clinical resource computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the clinical resource computing entity 105 with the assistance of the processing element 205 and operating system.

In one embodiment, the clinical resource computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery prediction system may be stored. Further, the information/data required for the operation of the recovery prediction system may also be partially stored in the cloud data storage system and partially stored in a locally maintained data storage system. More specifically, storage media 207 may encompass one or more data stores configured to store information/data usable in certain embodiments.

As indicated, in one embodiment, the clinical resource computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the clinical resource computing entity 105 may communicate with computing entities or communication interfaces of other clinical resource computing entities 105, user computing entities 101A-101N, and/or the like.

As indicated, in one embodiment, the clinical resource computing entity 105 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the clinical resource computing entity 105 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The clinical resource computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the clinical resource computing entity's components may be located remotely from other clinical resource computing entity 105 components, such as in a distributed system. Furthermore, one or more of the components may be aggregated and additional components performing functions described herein may be included in the clinical resource computing entity 105. Thus, the clinical resource computing entity 105 can be adapted to accommodate a variety of needs and circumstances.

B. Exemplary User Computing Entity

Figure 3:
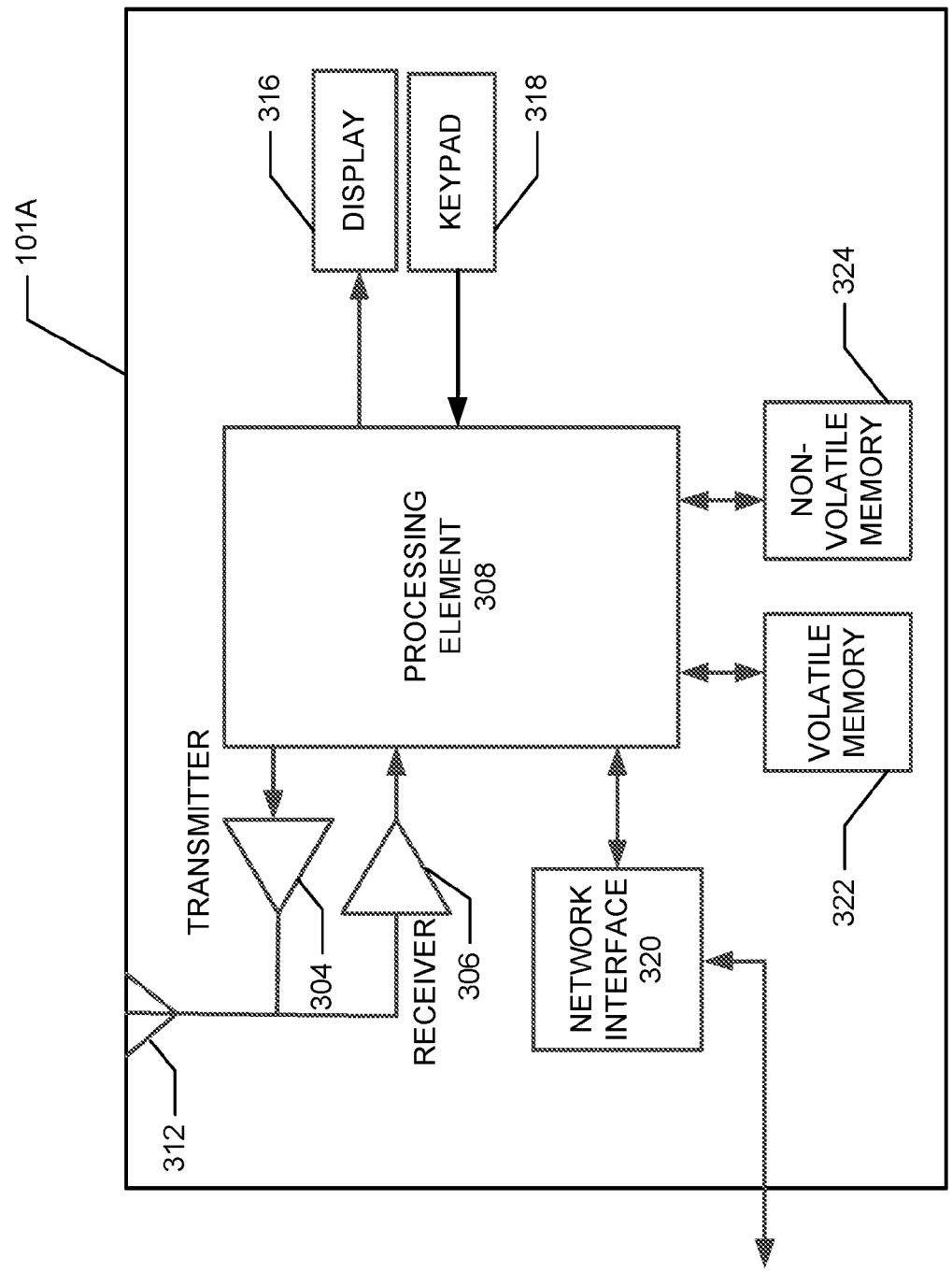
FIG. 3 is a schematic representation of an example user computing entity in accordance with various embodiments of the present disclosure.

FIG. 3 provides an illustrative schematic representative of one of the user computing entities 101A to 101N that can be used in conjunction with embodiments of the present disclosure. As will be recognized, the user computing entity may be operated by an agent and include components and features similar to those described in conjunction with the clinical resource computing entity 105. Further, as shown in FIG. 3, the user computing entity may include additional components and features. For example, the user computing entity 101A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a clinical resource computing entity 105, another user computing entity 101A, and/or the like. In this regard, the user computing entity 101A may be capable of operating with one or more air interface standards, communication protocols, modulation types, and access types. More particularly, the user computing entity 101A may comprise a network interface 320, and may operate in accordance with any of a number of wireless communication standards and protocols. In a particular embodiment, the user computing entity 101A may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 101A can communicate with various other entities using Unstructured Supplementary Service data (USSD), Short Message Service (SMS), Multimedia Messaging Service (MMS), Dual-Tone MultiFrequency Signaling (DTMF), Subscriber Identity Module Dialer (SIM dialer), and/or the like. The user computing entity 101A can also download changes, add-ons, and updates, for instance, to its firmware, software (e.g., including executable instructions, applications, program modules), and operating system.

According to one embodiment, the user computing entity 101A may include location determining aspects, devices, modules, functionalities, and/or similar words used herein interchangeably. For example, the user computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 101A to cause display or audible presentation of information/data and for user interaction therewith via one or more user input interfaces. The user output interface may be updated dynamically from communication with the clinical resource computing entity 105. The user input interface can comprise any of a number of devices allowing the user computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 101A can collect information/data, user interaction/input, and/or the like.

The user computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entities 101A-101N.

C. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JSON objects sent via a Websocket channel. In some embodiments, the protocol is JSON over RPC, JSON over REST/HTTP, and/or the like.

III. Exemplary Operation

Reference will now be made to FIGS. 4, 5, 6, 7, 8, 9, 10, 11, 12, 13, and 14. FIGS. 4, 5, 6, 7, 8, and 9 provide flowcharts illustrating example steps, processes, procedures, and/or operations associated with a clinical resource management platform/system in accordance with various embodiments of the present disclosure. FIGS. 10, 11, 12, 13, and 14 provide example views of interactive user interfaces in accordance with various embodiments of the present disclosure.

While example embodiments of the present disclosure may be described in the home healthcare context, as will be recognized, embodiments of the present invention are not limited to this context only.

A. Exemplary Service Value Point Balance Calculation

Figure 4:
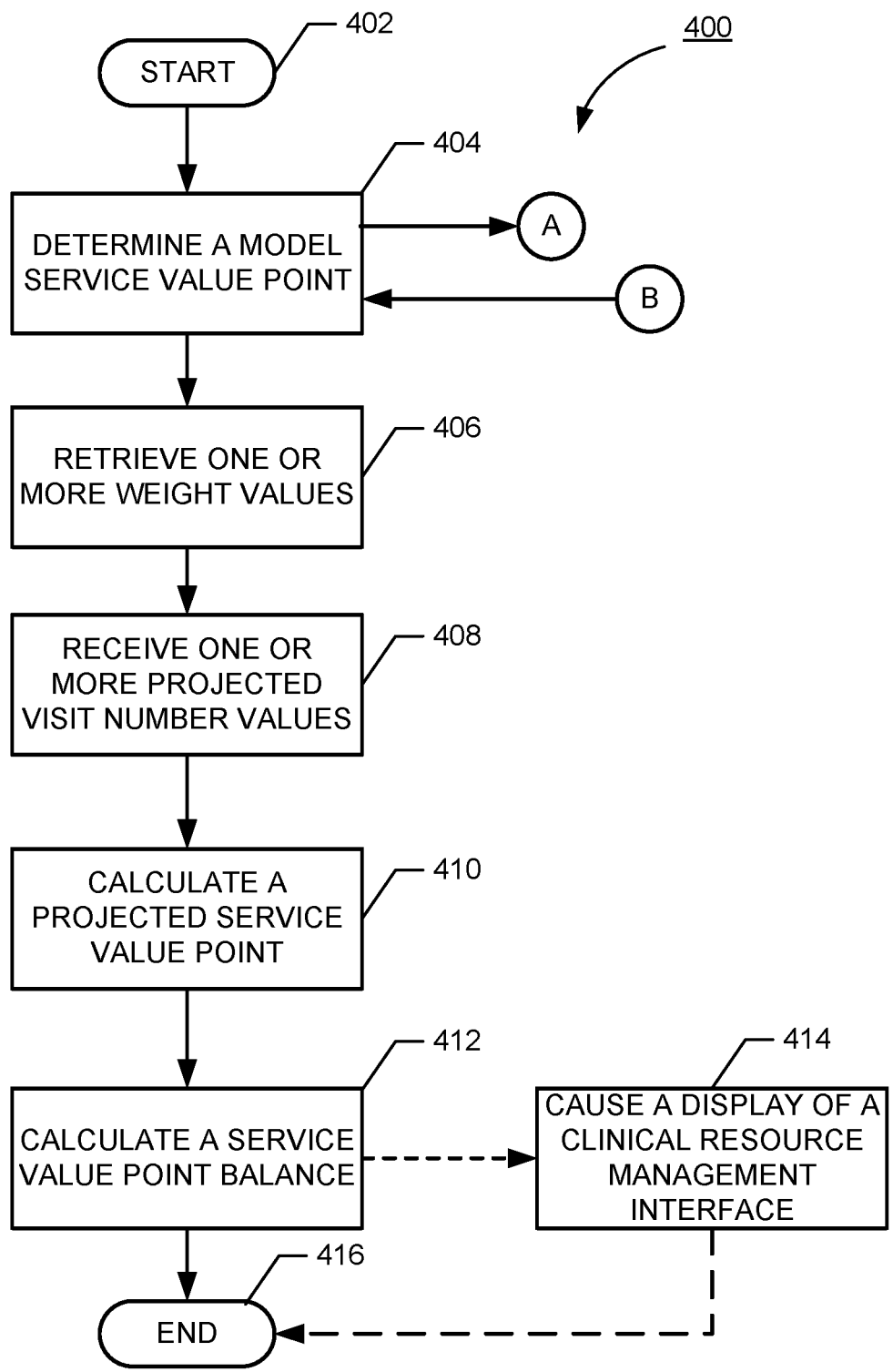

Referring now to FIG. 4, an example method 400 illustrates example calculations of example service value point balance in accordance with embodiments of the present disclosure.

The example method 400 may start at step/operation 402.

At step/operation 404, a computing entity (such as the clinical resource computing entity 105 described above in connection with FIG. 1 and FIG. 2) may include means (such as the processing element 205 of the clinical resource computing entity 105 described above in connection with FIG. 2) for determining a model service value point for a first patient episode.

The terms "patient episode" or "episode" may refer to a time duration or a time unit during which healthcare professional(s) may provide healthcare services to a patient. As described above, each episode may serve as a unit for calculating payment/reimbursement. For example, the pre-PDGM Home Health Prospective Payment System (HH PPS) defines each episode as having a 60-day window. Under PDGM, each episode has a 30-day window. It is noted that the scope of the present disclosure is not limited to 30-day episodes and 60-day episodes only, and an example episode of the present disclosure may have other length of time window.

The term "patient episode data" may refer to data, files, and other information associated with a patient episode, such as numbers of visits by different types of healthcare professionals (details of which are described herein). In an example embodiment, patient episode data for each patient may be generated and/or stored in a patient episode database and/or the like and accessible by the clinical resource computing entity 105, user computing entities 101A-101N, and/or the like. For example, one or more patient episode databases may be integrated within an example clinical resource management platform/system (such as the clinical resource management platform/system 100 described above in connection with FIG. 1). As another example, one or more patient episode databases may be integrated within one or more other databases (such as other databases described herein). As another example, one or more patient episode databases may be external to an example clinical resource management platform/system (such as the clinical resource management platform/system 100 described above in connection with FIG. 1).

In some embodiments, the patient episode data may be part of patient profile and stored in one or more patient profile databases. The term "patient profile" may refer to data, files, and other information associated with a patient, including, for example, a patient identifier, an email address, a real name (e.g., John Aaron), patient episode data, diagnosis data associated with the patient, and/or the like. The term "patient identifier" refers to an identifier that may uniquely identify information stored in a clinical resource management platform/system that is related to a patient.

In an example embodiment, a patient profile for each patient may be generated and/or stored in a patient profile database and/or the like and accessible by the clinical resource computing entity 105, user computing entities 101A-101N, and/or the like. For example, one or more patient profile databases may be integrated within an example clinical resource management platform/system (such as the clinical resource management platform/system 100 described above in connection with FIG. 1). As another example, one or more patient profile databases may be integrated within one or more other databases (such as other databases described herein). As another example, one or more patient profile databases may be external to an example clinical resource management platform/system (such as the clinical resource management platform/system 100 described above in connection with FIG. 1).

In some embodiments, a Home Health Resource Groups (HHRG) code may be associated with each episode. As described above, a HHRG code may be determined based on the results of OASIS.

In some embodiments, a HHRG code may be structured in accordance with the pre-PDGM HH PPS, which may comprise six numerical/alphabetical digits that range from C1F1S1 to C3F3S5, making a total of 153 possible HHRG codes. In such embodiments, the first two digits may indicate a clinical level, the next two digits may indicate a functional level, and the last two digits may indicate a service use category. For example, a HHRG code C3F3S1 may indicate a high clinical score ("C3"), a high functional score ("F3"), and one therapy visit (i.e. service utilization) ("S1"). As another example, a HHRG code C1F1S3 may indicate a low clinical score ("C1"), a low functional score ("F1"), and three therapy visits ("S3").

In some embodiments, a HHRG code be structed in accordance with the PDGM, which may comprise five numerical/alphabetical digits that range from 1AA11 to 4LC31, making a total of 432 possible HHRG codes. In such embodiments, the first digit may indicate score and timing, the second digit may indicate a clinical group, the third digit may indicate a functional level, the fourth digit may indicate co-morbidity, and the last digit may be a placeholder digit. For example, a HHRG code 1AA11 may indicate community source and early timing ("1"), a clinical group under Medication Management, Teaching and Assessment (MMTA) - Other ("A"), a low functional level ("A"), no co-morbidity ("1"), and a placeholder digit ("1"). As another example, a HHRG code 3AA11 may indicate community source and late timing ("3"), a clinical group under MMTA - Other ("A"), a low functional level ("A"), no co-morbidity ("1"), and a placeholder digit ("1").

While the above description provides example HHRG codes both pre-PDGM and under PDGM, it is noted that the scope of the present disclosure is not limited to these examples. In some embodiments, other models may be used to structure the HHRG code, including, but not limited to, Home Health Groupings Model (HHGM).

Referring back to FIG. 4, at step/operation 404, the model service value point may be determined based on the HHRG code associated with the patient episode. For example, a first patient episode may comprise a HHRG code that indicates the corresponding resource grouping of the first patient profile during the first episode (for example, C3F3S1 as described above).

The term "model service value point" refers to a numeric value that may indicate a benchmark resource allocation for a patient having a particular HHRG code during an episode. In some embodiments, a model service value point may be calculated or determined by a computing entity, such as the clinical resource computing entity 105 described above in connection with FIG. 1 and FIG. 2. Example embodiments of calculating/determining model service value points are described in connection with at least FIG. 6 and FIG. 7.

In an example embodiment, a model service value point for each HHRG code may be generated and/or stored in a model service value point database and/or the like and accessible by the clinical resource computing entity 105, user computing entities 101A-101N, and/or the like. For example, one or more model service value point databases may be integrated within an example clinical resource management platform/system (such as the clinical resource management platform/system 100 described above in connection with FIG. 1). As another example, one or more model service value point databases may be integrated within one or more other databases (such as other databases described herein). As another example, one or more model service value point databases may be external to an example clinical resource management platform/system.

At step/operation 406, a computing entity (such as the clinical resource computing entity 105 described above in connection with FIG. 1 and FIG. 2) may include means (such as the processing element 205 of the clinical resource computing entity 105 described above in connection with FIG. 2) for retrieving one or more weight values associated with one or more types of healthcare professional visits for the HHRG code.

A home healthcare provider may employ different types of healthcare professionals and may send these healthcare professionals to residences of patients to provide home healthcare services. Example healthcare professionals may include, but not limited to, home health aide, licensed practical nurse, registered nurse, medical social worker, physical therapy, physical therapy assistant, occupational therapist, certified occupational therapy assistant, and/or the like.

In some embodiments, each visit of a healthcare professional to a patient's residence may incur a resource cost. Example resource cost may include, but not limited to, work resources (for example, necessary equipment for the visit), monetary resources (for example, transportation cost), material resources (for example, consumable devices used during the visit), and/or the like.

In some embodiments, each of one or more weight values retrieved at step/operation 406 may indicate a resource cost associated with a particular type of clinical visit from a home healthcare provider to provide home healthcare services. In some embodiments, the higher the weight value, the higher the resource cost of a particular type of visit. For example, Table 1 below illustrates example weight values associated with different types of visits from different healthcare professionals for a patient with a HHRG code C3F3S1:

TABLE 1

Example Types of Visits and Example Weight Values

| Type of Healthcare Professional Who Visit (Type of Visit) | Weight Value |
|---|---|
| Home Health Aide (HHA) | 1.00 |
| Licensed Practical Nurse (LPN) | 1.52 |
| Registered Nurse (RN) | 2.33 |
| Admission | 4.31 |
| Recertification | 2.87 |
| Medical Social Worker (MSW) | 4.11 |
| Physical Therapist (PT) | 4.28 |
| Physical Therapist Assistant (PTA) | 2.82 |
| Occupational Therapist (OT) | 3.95 |
| Certified Occupational Therapy Assistant (COTA) | 2.82 |
| Speech-Language Therapist (ST) | 3.88 |

In the example as shown in Table 1, an HHA visit may have a corresponding weight value of 1.00, while an LPN visit may have a corresponding weight value of 1.52. In other words, an LPN visit to the patient with a HHRG code C3F3S1 may cost a home healthcare provider more resources than an HHA visit to this patient.

In an example embodiment, weight values for each type of visit may be generated and/or stored in a weight value database and/or the like and accessible by the clinical resource computing entity 105, user computing entities 101A-101N, and/or the like. For example, one or more weight value databases may be integrated within an example clinical resource management platform/system (such as the clinical resource management platform/system 100 described above in connection with FIG. 1). As another example, one or more weight value databases may be integrated within one or more other databases (such as other databases described herein). As another example, one or more patient profile databases may be external to an example clinical resource management platform/system (such as the clinical resource management platform/system 100 described above in connection with FIG. 1).

In some embodiments, weight values for each type of visit may be determined based on historical visit data associated with a home healthcare provider. For example, a computing entity (such as the clinical resource computing entity 105 described above in connection with FIG. 1 and FIG. 2) may analyze historical visit data, and may calculate a resource cost associated with each patient of the home healthcare provider. The computing entity may determine a HHRG code for each patient based on the historical visit data, identify the types of visits that each patient received, and calculate an average resource cost associated with each type of visit for each HHRG code. Based on the average resource cost, the computing entity may determine the corresponding weight value.

Additionally, or alternatively, other methodologies may be used to calculate the weight values. For example, a computing entity (such as the clinical resource computing entity 105 described above in connection with FIG. 1 and FIG. 2) may calculate a reimbursement rate for each type of visit and set a weight value based on the reimbursement rate. In some embodiments, the reimbursement rate may be an anticipated reimbursement rate for home health beneficiaries under the Medicare system.

At step/operation 408, a computing entity (such as the clinical resource computing entity 105 described above in connection with FIG. 1 and FIG. 2) may include means (such as the processing element 205 of the clinical resource computing entity 105 described above in connection with FIG. 2) for receiving one or more actual visit numbers and/or one or more projected visit numbers associated with the first patient episode.

The term "actual visit number" refers to a number of actual visits by a particular type of healthcare professional of a home healthcare provider for providing home healthcare services to a patient. In some embodiments, the actual visit number may be stored as part of a patient profile associated with a patient. For example, if a patient profile indicates that an actual LPN visit number is 9, the patient corresponding to the patient profile have received 9 visits from a license practical nurse of the home healthcare provider.

The term "projected visit number" refers to a number of estimated or forecasted visits by a particular type of healthcare professional of a home healthcare provider for providing home healthcare services to a patient. In some embodiments, the projected visit number may be stored as part of a patient profile associated with a patient. For example, a projected PT visit number of 3 may indicate that 3 visits from a physical therapist is projected for this patient.

In some embodiments, a user (such as a home healthcare administrator) may provide the actual visit numbers and/or the projected visit numbers associated with the first patient episode/profile to an example clinical resource computing entity (such as the clinical resource computing entity 105 described above in connection with FIG. 1 and FIG. 2) using a user computing entity (such as the user computing entities 101A to 101N described above in connection with FIG. 1 and FIG. 3). In some embodiments, an example clinical resource computing entity (such as the clinical resource computing entity 105 described above in connection with FIG. 1) may generate one or more user interface elements (such as an input box) to request the actual visit numbers and/or the projected visit numbers. Example user interfaces are illustrated and described in connection with at least FIG. 10 to FIG. 14.

In some embodiments, the projected visit numbers may be determined through machine learning models, such as, but not limited to, those based on predictive modeling techniques. For example, a computing entity (such as the clinical resource computing entity 105 described above in connection with FIG. 1 and FIG. 2) may perform regression analysis to determine a relationship between historical visit numbers associated with the corresponding HHRG code and the actual visit number associated with this particular episode. In performing the regression analysis (such as linear regression), the computing entity may determine a regression line that predicts a likely (or projected) visit number for this episode.

Referring back to FIG. 4, at step/operation 410, a computing entity (such as the clinical resource computing entity 105 described above in connection with FIG. 1 and FIG. 2) may include means (such as the processing element 205 of the clinical resource computing entity 105 described above in connection with FIG. 2) for calculating a projected service value point based at least in part on the one or more weight values and the one or more projected visit numbers.

The term "projected service value point" refers to a numeric value that may indicate a projected resource allocation for a patient having a particular HHRG code.

In some embodiments, the computing entity (such as the clinical resource computing entity 105 described above in connection with FIG. 1 and FIG. 2) may calculate the projected service value point by multiplying each projected visit number with a weight value based on the type of visit, and then adding the results of these multiplications together. For example, an example calculation of an example projected service value point may be based on the following formula:

$$PSVP = \sum_{i=1}^{n}(P_i \times W_i)$$

In the above formula, PSVP represents the projected service value point, $P_i$ represents a projected visit number, and $W_i$ represents a weight value for the corresponding projected visit number. As an example, Table 2 below illustrates example sets of projected visit numbers and their corresponding weight values:

TABLE 2

Example Projected Visit Numbers and Example Weight Values

| Type of Visit | Projected Visit number | Weight Value |
| --- | --- | --- |
| HHA | 0 | 1.00 |
| LPN | 2 | 1.52 |
| RN | 0 | 2.33 |
| Admission | 0 | 4.31 |
| Recertification | 0 | 2.87 |
| MSW | 0 | 4.11 |
| PT | 3 | 4.28 |
| PTA | 0 | 2.82 |

TABLE 2-continued

Example Projected Visit Numbers and Example Weight Values

| Type of Visit | Projected Visit number | Weight Value |
| --- | --- | --- |
| OT | 0 | 3.95 |
| COTA | 0 | 2.82 |
| ST | 0 | 3.88 |

In the example shown in Table 2, the corresponding projected service value point (PSVP) may be calculated based on the following:

$$PSVP = 0 \times 1.00 + 2 \times 1.52 + 0 \times 2.33 + 0 \times 4.31 + 0 \times 2.87 + 0 \times 4.11 + 3 \times 4.28 \\ + 0 \times 2.82 + 0 \times 3.95 + 0 \times 2.82 + 0 \times 3.88 = 15.88$$

In this example, the projected service value point is 15.88.

As described above, weight values may be determined based on a resource cost associated with a particular type of clinical visit from a home healthcare provider to provide home healthcare services. In some embodiments, weight values may be determined manually based on, for example, compensation data associated with the healthcare professional who provides the home healthcare service.

In some embodiments, weight values may be determined based on, for example, machine learning models. The term "machine learning model" refers to a computer algorithm that may perform one or more specific tasks through pattern/interference recognition and without the need for explicit instructions. Example machine learning models may include, but not limited to, deep learning models, ensemble models, regression models, and/or the like.

For example, a computing entity (such as the clinical resource computing entity 105 described above in connection with FIG. 1 and FIG. 2) may implement a linear regression model to determine the correlation between each type of visit and the cost associated with each visit during an episode. Based on the correlation, the linear regression model may generate one or more weight values that may indicate the corresponding resource cost.

Additionally, or alternatively, the computing entity (such as the clinical resource computing entity 105 described above in connection with FIG. 1 and FIG. 2) may include means (such as the processing element 205 of the clinical resource computing entity 105 described above in connection with FIG. 2) for calculating a projected service value point based at least in part on the one or more weight values, the one or more actual visit numbers, and the one or more projected visit numbers.

In some embodiments, the computing entity (such as the clinical resource computing entity 105 described above in connection with FIG. 1 and FIG. 2) may calculate the projected service value point by adding each actual visit number with each projected visit number based on the type of visit, multiplying the results of these additions with a weight value based on the type of visit, and then adding the results of these multiplications together. For example, an example calculation of an example projected service value point may be based on the following formula:

$$PSVP = \sum_{i=1}^{n}((A_i + P_i) \times W_i)$$

In the above formula, PSVP represents the projected service value point, $A_i$ represents an actual visit number, $P_i$ represents a projected visit number, and $W_i$ represents a weight value for the corresponding projected visit number. As an example, Table 3 below illustrates example sets of actual visit numbers, projected visit numbers and their corresponding weight values:

TABLE 3

Example Actual Visit Numbers, Example Projected Visit Numbers and Example Weight Values

| Type of Visit | Actual Visit Number | Projected Visit Number | Weight Value |
| --- | --- | --- | --- |
| HHA | 1 | 0 | 1.00 |
| LPN | 0 | 2 | 1.52 |
| RN | 0 | 0 | 2.33 |
| Admission | 0 | 0 | 4.31 |
| Recertification | 0 | 0 | 2.87 |
| MSW | 0 | 0 | 4.11 |
| PT | 0 | 3 | 4.28 |
| PTA | 1 | 0 | 2.82 |
| OT | 0 | 0 | 3.95 |
| COTA | 0 | 0 | 2.82 |
| ST | 0 | 0 | 3.88 |

In the example shown in Table 3, the corresponding projected service value point (PSVP) may be calculated based on the following:

$$PSVP = (1+0) \times 1.00 + (0+2) \times 1.52 + (0+0) \times 2.33 + (0+0) \times 4.31 \\ + (0+0) \times 2.87 + (0+0) \times 4.11 + (0+3) \times 4.28 + (1+0) \times 2.82 \\ + (0+0) \times 3.95 + (0+0) \times 2.82 + (0+0) \times 3.88 = 19.7$$

In this example, the projected service value point is 19.7.

Additionally, or alternatively, the computing entity (such as the clinical resource computing entity 105 described above in connection with FIG. 1 and FIG. 2) may include means (such as the processing element 205 of the clinical resource computing entity 105 described above in connection with FIG. 2) for determining at least one machine learning model based on the patient profile for calculating projected service value points, and may calculate the projected service value point based at least in part on the one or more weight values, the plurality of projected visit numbers, and the at least one machine learning model.

In some embodiments, the computing entity may select a machine learning model based on a HHRG code associated with the patient profile. For example, the computing entity may provide the one or more weight values and the plurality of projected visit numbers as inputs to a deep learning network. The deep learning network may be trained using episode data associated with the HHRG code, and may generate an output that indicates the projected service value point.

At step/operation 412, a computing entity (such as the clinical resource computing entity 105 described above in connection with FIG. 1 and FIG. 2) may include means (such as the processing element 205 of the clinical resource computing entity 105 described above in connection with FIG. 2) for calculating a service value point balance based at least in part on the model service value point and the projected service value point.

In some embodiments, the computing entity may calculate the service value point balance by subtracting the projected service value point from the model service value point. For example, an example calculation of an example service value point balance may be based on the following formula:

$$SVPB = MSVP - PSVP$$

In the above formula, SVPB represents the service value point balance, MSVP represents the model service value point, and PSVP represents the projected service value point. For example, if the model service value point (determined at step/operation 404) is 22.9 and the projected service value point (calculated at step/operation 410) is 19.7, the service value point balance calculated at step/operation 412 may be 22.9 - 19.7 = 3.2.

In some embodiments, the service value point balance may indicate a corresponding remaining amount of resource based on what the healthcare provider has allocated to the patient for a given episode and what resource the patient has consumed during the episode. The higher the service value point, the more resource that is available to serve the patient. In the aggregate, the healthcare provider may use the service value point balance as a guidance in allocating resource for a particular patient.

At step/operation 414, a computing entity (such as the clinical resource computing entity 105 described above in connection with FIG. 1 and FIG. 2) may include means (such as the processing element 205 of the clinical resource computing entity 105 described above in connection with FIG. 2) for causing a display of a clinical resource management interface.

In some embodiments, the clinical resource management interface may be rendered on a display of a clinical resource computing entity (such as the clinical resource computing entity 105 described above in connection with FIG. 1 and FIG. 2). In some embodiments, the clinical resource management interface may be rendered on a display of a user computing entity (such as the user computing entities 101A-101N described above in connection with FIG. 1 and FIG. 3).

Figure 10:
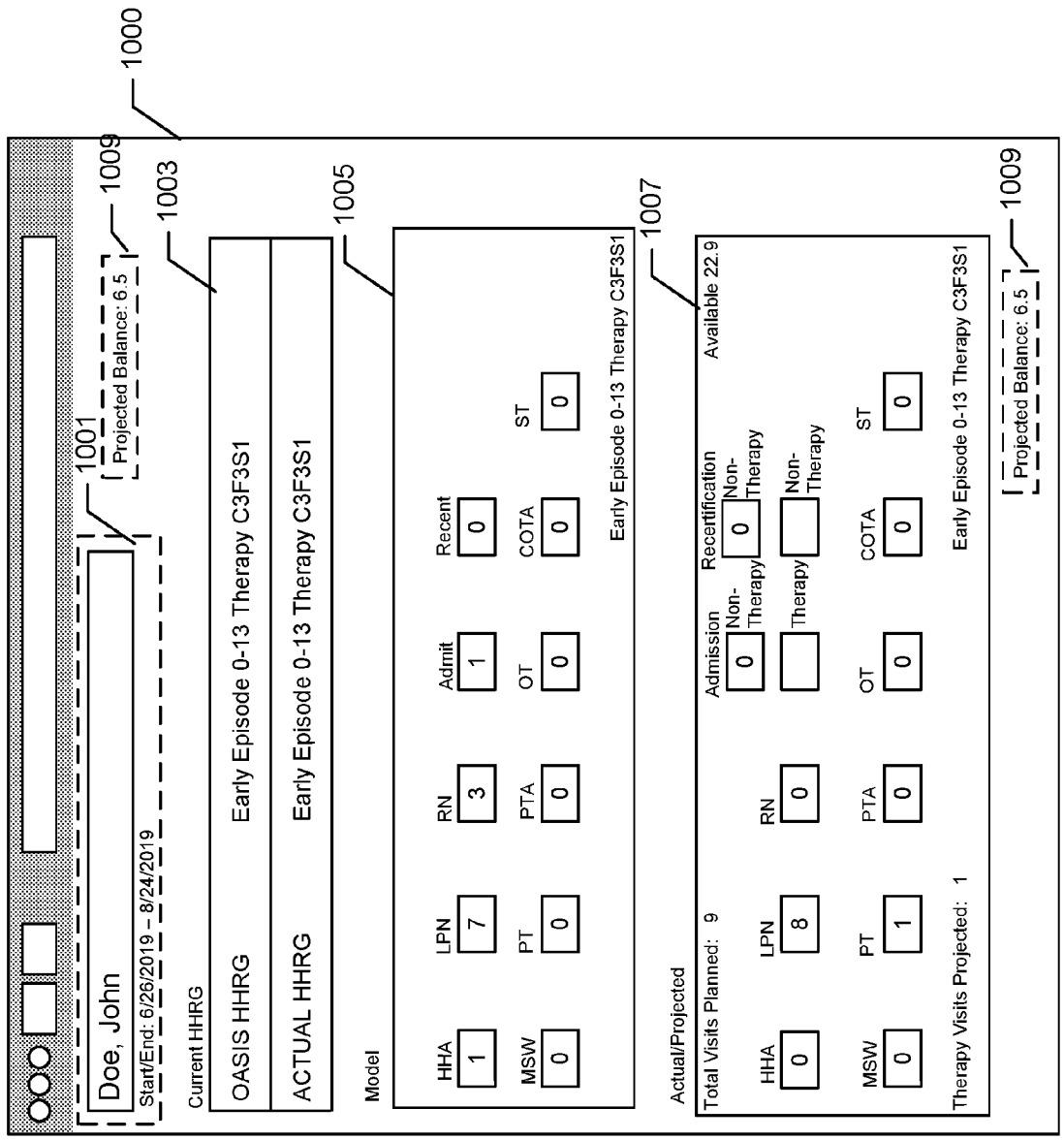

Referring now to FIG. 10, an example user interface 1000 is illustrated. In FIG. 10, the user interface 1000 may comprise a header section 1001, which may indicate a name associated with a patient based on, for example, the corresponding patient profile. Additionally, or alternatively, the header section 1001 may indicate the starting/ending date of an episode associated with the patient.

In some embodiments, the example user interface 1000 may comprise a HHRG information section 1003, which may provide the corresponding HHRG code associated with the episode. In the example shown in FIG. 10, the HHRG information section 1003 may comprise an OASIS HHRG section and an actual HHRG section, which may provide the HHRG based on the results of OASIS and the actual HHRG, respectively. In some embodiments, the HHRG information section 1003 may also list a current service value point balance associated with the patient (for example, 10.8 as shown in FIG. 10).

In some embodiments, the example user interface 1000 may comprise a benchmark section 1005, which may provide one or more model visit numbers associated with different types of visits for the particular episode. In the example shown in FIG. 10, the benchmark section 1005 illustrates a model visit number 1 for HHA, which indicates that a computing entity (such as the clinical resource computing entity 105 described above in connection with FIG. 1 and FIG. 2) may determine that one visit from an HHA may optimize the resource allocation of the home healthcare provider. In some embodiments, based on model visit numbers associated with different types of visits, the computing entity may determine the model service value point, details of which are described in connection with at least FIG. 6.

In some embodiments, the example user interface 1000 may comprise an actual/project section 1007, which may provide one or more actual visit numbers and/or one or more projected visit numbers. In the example as shown in FIG. 10, the actual/project section 1007 illustrates a projected visit number 1 for PT, which indicates that a computing entity (such as the clinical resource computing entity 105 described above in connection with FIG. 1 and FIG. 2) may have received an input from a user operating a user computing entity (for example, user computing entities 101A-101N described above in connection with FIG. 1 and FIG. 3) indicating a projected visit number for PT, as described above in connection with step/operation 408.

In some embodiments, the actual/project section 1007 may use different colors to distinguish actual/planned visits from projected visits. For example, the actual visit numbers may be rendered in a first color, and the projected visit numbers may be rendered in a second color that is different from the first color.

In some embodiments, the actual/project section 1007 may provide a summary of a total number of actual/planned visits (for example, 9 in the example shown in FIG. 10) and/or a summary of a total number of projected visits (for example, 1 in the example shown in FIG. 10).

In some embodiments, the example user interface 1000 may comprise one or more projected service value point sections 1009, which may provide the projected service value point. In some embodiments, the projected service value point may be calculated based on step/operation 412 described above.

Referring back to FIG. 4, the example method 400 may end at step/operation 416.

Figure 5:
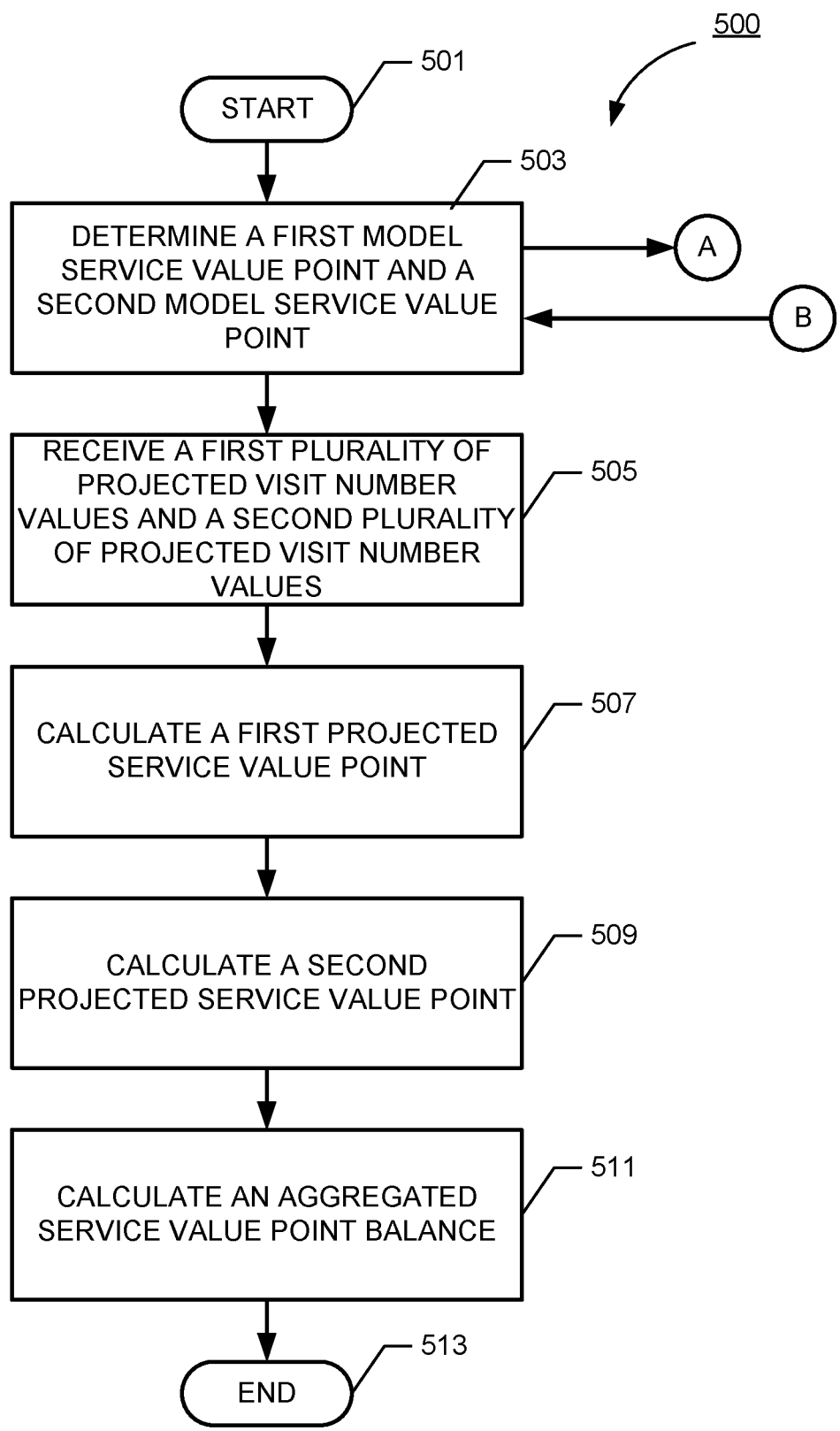

Referring now to FIG. 5, an example method 500 illustrates operation of example calculations of example service value point balance in accordance with embodiments of the present disclosure.

The example method 500 may start at step/operation 501.

At step/operation 503, a computing entity (such as the clinical resource computing entity 105 described above in connection with FIG. 1 and FIG. 2) may include means (such as the processing element 205 of the clinical resource computing entity 105 described above in connection with FIG. 2) for determining a first model service value point and a second model service value point associated with a patient profile.

In some embodiments, the first model service value point may be associated with a first time period and the second model service value point may be associated with a second time period. As described above, PDGM provides a 30-day episode instead of a 60-day episode. The first time period may be the first 30-day period of home healthcare services to the patient (i.e. the first episode), and the second time period may be a subsequent 30-day period of home healthcare services to the patient (i.e. a later episode).

In some embodiments, the first model service value point and/or the second model service value point may be determined similar to those described above in connection with FIG. 4 and below in connection with FIG. 6 and FIG. 7.

At step/operation 505, a computing entity (such as the clinical resource computing entity 105 described above in connection with FIG. 1 and FIG. 2) may include means (such as the processing element 205 of the clinical resource computing entity 105 described above in connection with FIG. 2) for receiving a first plurality of actual or projected visit numbers associated with the first time period and a second plurality of actual or projected visit numbers associated with the second time period.

As described above, the first time period may be associated with the first 30 days of home healthcare services to the patient. In such an example, the first plurality of actual or projected visit numbers may be associated with actual or projected visits to the patient during the first 30-day window. Similarly, the second time period may be associated with a subsequent 30 days of home healthcare services to the patient, and the second plurality of actual or projected visit numbers may be associated with actual or projected visits to the patient during a subsequent 30-day window.

In some embodiments, the first plurality of actual or projected visit numbers and/or the second plurality of actual or projected visit numbers may be received from one or more users operating one or more user computing entities (such as the user computing entities 101A to 101N described above in connection with FIG. 1 and FIG. 3), similar to those described above in connection with step/operation 408 of FIG. 4.

At step/operation 507, a computing entity (such as the clinical resource computing entity 105 described above in connection with FIG. 1 and FIG. 2) may include means (such as the processing element 205 of the clinical resource computing entity 105 described above in connection with FIG. 2) for calculating a first projected service value point based at least in part on the one or more weight values and the first plurality of projected visit numbers.

In some embodiments, the computing entity may calculate the first projected service value point similar to those described above in connection with step/operation 410 of FIG. 4. For example, the computing entity may multiply the first plurality of projected visit numbers with their corresponding weight values based on the type of visit and may add the results of multiplications. The sum may be the first projected service value point.

In some embodiments, the calculation of the first projected service value point may be based at least in part on the one or more weight values, the first plurality of projected visit numbers, and at least one machine learning model, similar to those described above in connection with step/operation 410 of FIG. 4.

At step/operation 509, a computing entity (such as the clinical resource computing entity 105 described above in connection with FIG. 1 and FIG. 2) may include means (such as the processing element 205 of the clinical resource computing entity 105 described above in connection with FIG. 2) for calculating a second projected service value point based at least in part on the one or more weight values and the second plurality of projected visit numbers.

In some embodiments, the computing entity may calculate the second projected service value point similar to those described above in connection with step/operation 410 of FIG. 4. For example, the computing entity may multiply the second plurality of projected visit numbers with their corresponding weight values based on the type of visit and may add the results of multiplications. The sum may be the second projected service value point.

In some embodiments, the calculation of the second projected service value point may be based at least in part on the one or more weight values, the second plurality of projected visit numbers, and at least one machine learning model, similar to those described above in connection with step/operation 410 of FIG. 4.

At step/operation 511, a computing entity (such as the clinical resource computing entity 105 described above in connection with FIG. 1 and FIG. 2) may include means (such as the processing element 205 of the clinical resource computing entity 105 described above in connection with FIG. 2) for calculating an aggregated service value point balance based at least in part on the first model service value point, the first projected service value point, the second model service value point, and the second projected service value point.

In some embodiments, the computing entity may calculate the aggregated service value point balance based on the following formula:

$$ASVPB = (MSVP_1 - PSVP_1) + (MSVP_2 - PSVP_2)$$

In the above formula, ASVPB refers to the aggregated service value point balance, $MSVP_1$ is the first model service value point, $PSVP_1$ is the first projected service value point, $MSVP_2$ is the second model service value point, and $PSVP_2$ is the second projected service value point. In some embodiments, other formulas may be used to calculate the aggregated service value point balance.

In some embodiments, a computing entity (such as the clinical resource computing entity 105 described above in connection with FIG. 1 and FIG. 2) may include means (such as the processing element 205 of the clinical resource computing entity 105 described above in connection with FIG. 2) for causing a display of a clinical resource management interface. Similar to those described above in connection with step/operation 414 of FIG. 4, the clinical resource management interface may be rendered on a display of a clinical resource computing entity (such as the clinical resource computing entity 105 described above in connection with FIG. 1 and FIG. 2), and/or on a display of a user computing entity (such as the user computing entities 101A-101N described above in connection with FIG. 1 and FIG. 3).

Figure 11:
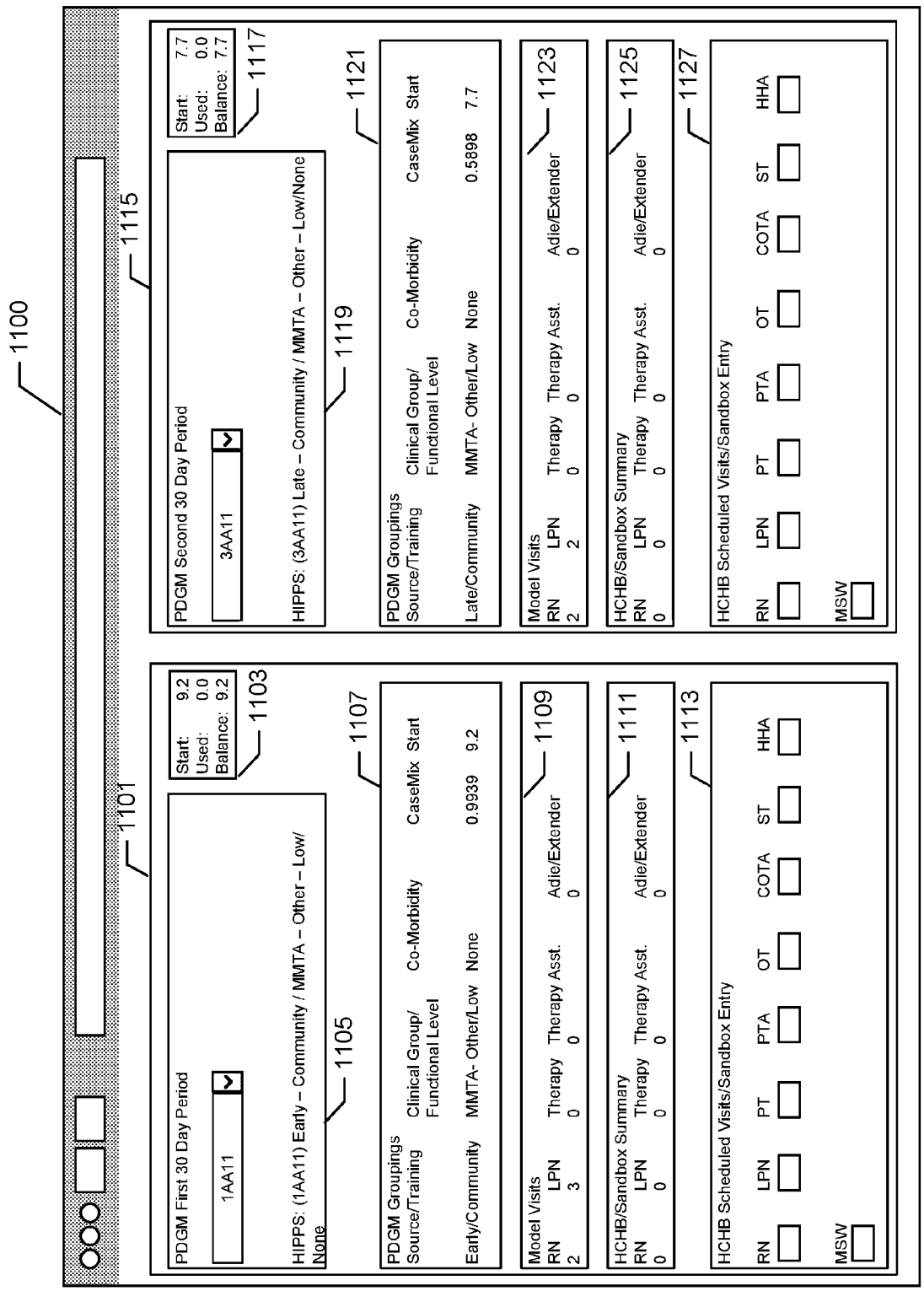

Referring now to FIG. 11, an example user interface 1100 is illustrated. In FIG. 11, the example user interface 1100 may comprise a first window portion 1101 and a second window portion 1115.

In some embodiments, the first window portion 1101 may comprise a first header section 1105, which may indicate the first time period and a first HHRG code associated with the patient profile. For example, the first time period may be the first 30-day period of providing home healthcare services to the patient.

In some embodiments, the first window portion 1101 may comprise a first summary section 1103, which may indicate the first model service value point, the first projected service value point, and/or the first service value point balance. The first model service value point, the first projected service value point, and the first service value point balance may be associated with a first time period (as shown in the first header section 1105). The first service value point balance may be calculated based on subtracting the first projected service value point from the first model service value point. In the example shown in FIG. 11, the first summary section 1103 may indicate a first model service value point of 9.2, a first projected service value point of 0.0, and a first service value point balance 9.2.

In some embodiments, the first window portion 1101 may comprise a first HHRG description section 1107. The first HHRG description section 1107 may, for example, provide description of the episode under PDGM during the first time period.

In some embodiments, the first window portion 1101 may comprise a first benchmark section 1109. Similar to the benchmark section 1005 described above in connection with FIG. 10, the first benchmark section 1109 may provide one or more model visit numbers associated with the particular HHRG as shown in the first header section 1105 and described in the first HHRG description section 1107.

In some embodiments, the first window portion 1101 may comprise a first sandbox summary section 1111, which may provide one or more actual visit numbers associated with the particular patient during the first time period.

In some embodiments, the first window portion 1101 may comprise a first projected section 1113, which may provide one or more projected visit numbers associated with the particular patient during the first time period.

In some embodiments, the second window portion 1115 may comprise a second header section 1119, which may indicate the second time period and a second HHRG code associated with the patient profile. For example, the second time period may be the second 30-day period of providing home healthcare services to the patient.

In some embodiments, the second window portion 1115 may comprise a second summary section 1117, which may indicate the second model service value point, the second projected service value point, and/or the second service value point balance. The second model service value point, the second projected service value point, and the second service value point balance may be associated with a second time period (as shown in the second header section 1119). The second service value point balance may be calculated based on subtracting the second projected service value point from the second model service value point. In the example shown in FIG. 11, the second summary section 1117 may indicate a second model service value point of 7.7, a second projected service value point of 0.0, and a second service value point balance 7.7.

In some embodiments, the second window portion 1115 may comprise a second HHRG description section 1121. The second HHRG description section 1121 may, for example, provide description of the episode under PDGM during the second time period.

In some embodiments, the second window portion 1115 may comprise a second benchmark section 1123. Similar to the benchmark section 1005 described above in connection with FIG. 10, the second benchmark section 1123 may provide one or more model visit numbers associated with the particular HHRG as shown in the second header section 1119 and described in the second HHRG description section 1121.

In some embodiments, the second window portion 1115 may comprise a second sandbox summary section 1125, which may provide one or more actual visit numbers associated with the particular patient during the second time period.

In some embodiments, the second window portion 1115 may comprise a second projected section 1127, which may provide one or more projected visit numbers associated with the particular patient during the second time period.

Referring back to FIG. 5, the example method 500 may end at step/operation 513.

B. Exemplary Model Service Value Points Determination

Figure 6:
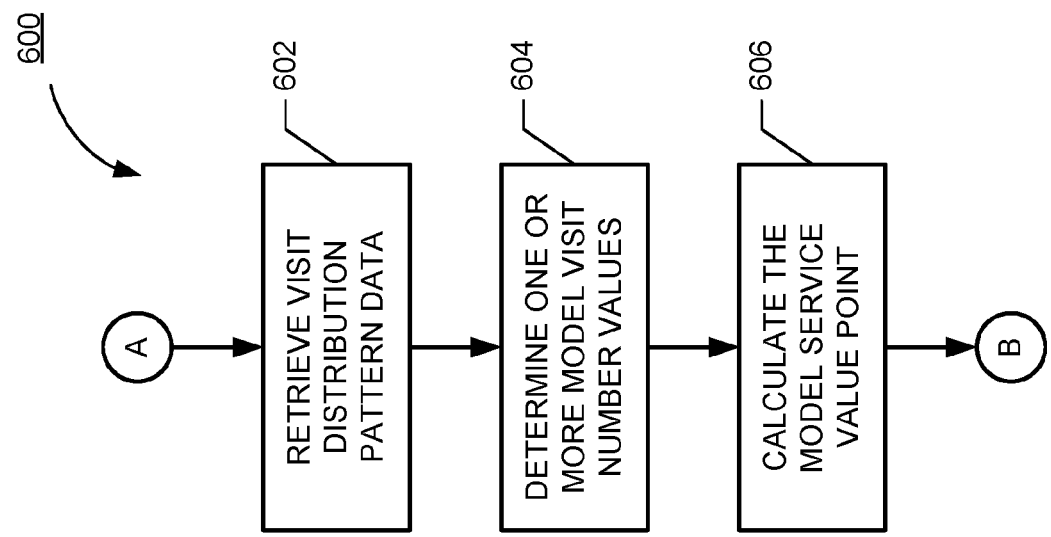

Referring now to FIG. 6, an example method 600 illustrates operation of determining model service value points in accordance with embodiments of the present disclosure.

At step/operation 602, a computing entity (such as the clinical resource computing entity 105 described above in connection with FIG. 1 and FIG. 2) may include means (such as the processing element 205 of the clinical resource computing entity 105 described above in connection with FIG. 2) for retrieving visit distribution pattern data associated with a home healthcare provider.

The term "visit distribution pattern data" refer to data, files, and other information associated with visits by healthcare professionals of a home healthcare provider to provide home healthcare services to patients. In some embodiments, the visit distribution pattern data may categorize these visits based on the types of healthcare professional visit and the HHRG code associated with a patient. For example, the visit distribution pattern data may indicate an HHA visit number, an LPN visit number, a RN visit number, and the like that are associated with a patient having a particular HHRG code (for example, C3F3S1).

In an example embodiment, visit distribution pattern data for home healthcare providers may be generated and/or stored in a visit distribution pattern database and/or the like and accessible by the clinical resource computing entity 105, user computing entities 101A-101N, and/or the like. For example, one or more visit distribution pattern databases may be integrated within an example clinical resource management platform/system (such as the clinical resource management platform/system 100 described above in connection with FIG. 1). As another example, one or more visit distribution pattern databases may be integrated within one or more other databases (such as other databases described herein). As another example, one or more visit distribution pattern databases may be external to an example clinical resource management platform/system (such as the clinical resource management platform/system 100 described above in connection with FIG. 1).

In some embodiments, the visit distribution pattern data may be integrated with historical data, and/or may be generated automatically based on one or more machine learning models. For example, a computing entity (such as the clinical resource computing entity 105 described above in connection with FIG. 1 and FIG. 2) may implement a deep neural network to recognize distribution patterns associated with patient visits. In this example, the computing entity may provide historical data associated with patient visits (for example, the type of visit, the frequency of visit, the number of visits) as an input to the deep neural network, and may receive visit distribution pattern data as an output.

In some embodiments, historical data may be stored in a historical database and/or the visit distribution pattern database and/or the like and accessible by the clinical resource computing entity 105, user computing entities 101A-101N, and/or the like so that it may be accessible by the clinical resource computing entity 105, user computing entities 101A-101N, and/or the like.

At step/operation 604, a computing entity (such as the clinical resource computing entity 105 described above in connection with FIG. 1 and FIG. 2) may determine one or more model visit numbers based on the visit distribution pattern data.

In some embodiments, the computing entity may derive the one or more model visit numbers based on calculating an average number of visits from a particular type of healthcare professional for a particular type of HHRG code. Continuing from the example above, the computing entity may calculate an average number of RN visits based on the visit distribution pattern data for HHRG code C3F3S1, and may use the average number as the model visit number for the RN visit for HHRG code C3F3S1. In some embodiments, the computing entity may calculate a mode number of the RN visits based on the visit distribution pattern data for HHRG code C3F3S1, and may use the mode number as the model visit number for the RN visit for HHRG code C3F3S1. In some embodiments, other statistic number(s) may be used as the model visit number.

In some embodiments, the computing entity may derive the one or more model visit numbers based on one or more machine learning algorithms. For example, the computing entity may implement pattern recognition techniques (such as supervised or unsupervised learning algorithms), data mining algorithms (such as artificial neural networks, decision tree algorithms), and/or the like for identifying an optimum number of visits from each type of healthcare professional for each HHRG code. For example, the computing entity may implement a decision tree algorithm to determine one or more model visit numbers based on the visit distribution pattern data. In a decision tree, each node may represent a feature (for example, an attribute associated with the visit distribution data), each branch may represent a decision (for example, a threshold value), and each leaf may represent an outcome (for example, the optimum number of visits). The computing entity may provide the visit distribution pattern data as the input (i.e. top of the tree). Through filtering by one or more layers of branches, the decision tree may produce an outcome that correspond to a model visit number for a particular type of visit for a particular HHRG code.

At step/operation 606, a computing entity (such as the clinical resource computing entity 105 described above in connection with FIG. 1 and FIG. 2) may include means (such as the processing element 205 of the clinical resource computing entity 105 described above in connection with FIG. 2) for calculating the model service value point for the first patient profile based at least in part on the one or more model visit numbers and the one or more weight values.

In some embodiments, the computing entity (such as the clinical resource computing entity 105 described above in connection with FIG. 1 and FIG. 2) may calculate the model service value point by multiplying each model visit number with a weight value based on the type of visit, and then adding the results of these multiplications together. For example, an example calculation of an example model service value point may be based on the following formula:

$$MSVP = \sum_{i=1}^{n}(M_i \times W_i)$$

In the above formula, MSVP represents the model service value point, $M_i$ represents a model visit number, and $W_i$ represents a weight value for the corresponding model visit number. As an example, Table 4 below illustrates example sets of model visit numbers and their corresponding weight values:

TABLE 4

Example Model Visit Numbers and Example Weight Values

| Type of Visit | Model Visit number | Weight Value |
|---|---|---|
| HHA | 1 | 1.00 |
| LPN | 7 | 1.52 |
| RN | 3 | 2.33 |
| Admission | 1 | 4.31 |
| Recertification | 0 | 2.87 |
| MSW | 0 | 4.11 |
| PT | 0 | 4.28 |
| PTA | 0 | 2.82 |
| OT | 0 | 3.95 |
| COTA | 0 | 2.82 |
| ST | 0 | 3.88 |

In the example shown in Table 4, the corresponding model service value point (MSVP) may be calculated based on the following:

$$MSVP = 1 \times 1.00 + 7 \times 1.52 + 3 \times 2.33 + 1 \times 4.31 + 0 \times 2.87 \\ + 0 \times 4.11 + 0 \times 4.28 + 0 \times 2.82 + 0 \times 3.95 + 0 \times 2.82 \\ + 0 \times 3.88 = 22.94$$

In this example, the model service value point is 22.94.

Figure 7:
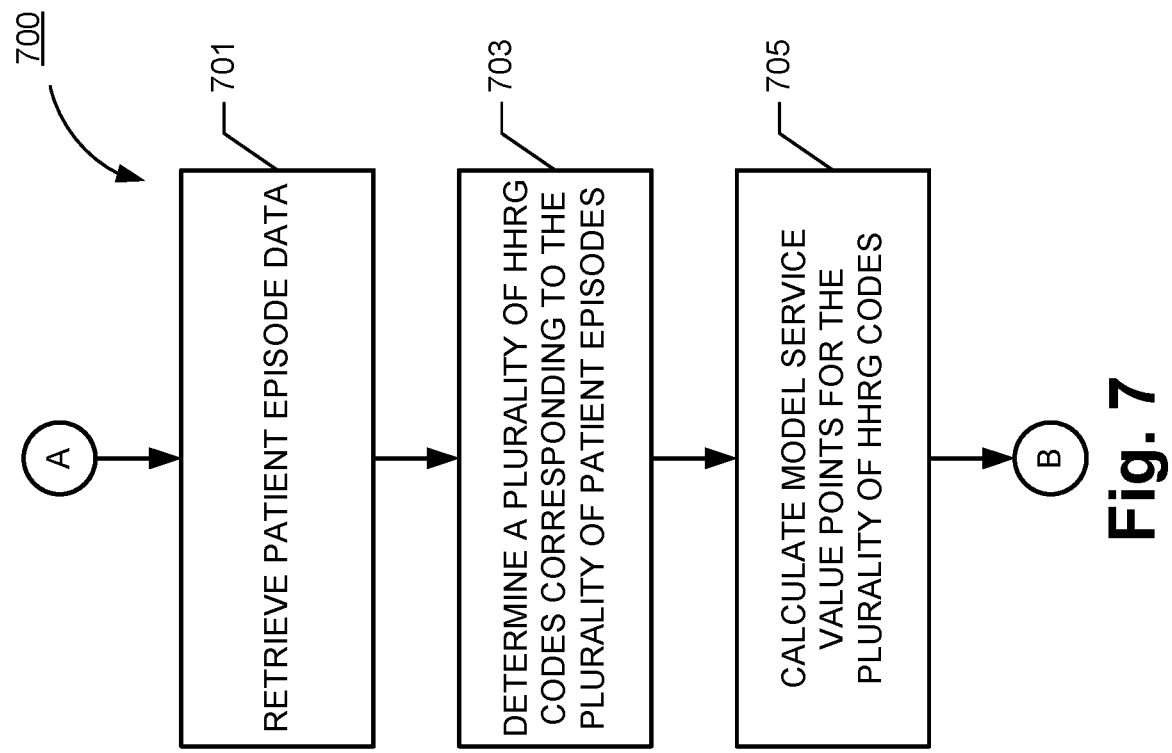

Referring now to FIG. 7, an example method 700 illustrates operation of determining model service value points in accordance with embodiments of the present disclosure. As described above, regulatory change to PDGM has rendered many methods obsolete, causing technical challenges in setting benchmarks for allocating clinical resource under the PDGM. The example method 700 described herein may overcome these challenges.

At step/operation 701, a computing entity (such as the clinical resource computing entity 105 described above in connection with FIG. 1 and FIG. 2) may include means (such as the processing element 205 of the clinical resource computing entity 105 described above in connection with FIG. 2) for retrieving patient episode data corresponding to a plurality of patient episodes associated with the home healthcare provider.

In some embodiments, the patient episode data may be part of patient profile and stored in one or more patient profile databases. In some embodiments, the patient episode data may describe one or more patient episodes associated with a patient. For example, the patient episode data may comprise episode descriptors, which may describe the details of each episode associated with the patient, such as (but not limited to), admission source of the patient (e.g. institutional or community), functional impairment levels, secondary diagnoses, and/or the like.

At step/operation 703, a computing entity (such as the clinical resource computing entity 105 described above in connection with FIG. 1 and FIG. 2) may include means (such as the processing element 205 of the clinical resource computing entity 105 described above in connection with FIG. 2) for determining, based on the episode descriptors, a plurality of HHRG codes corresponding to the plurality of patient episodes under the PDGM.

In some embodiments, the computing entity may implement one or more machine learning algorithms to categorize each patient episode to one of the groupings under PDGM. For example, the computing entity may implement a recurrent neural network (RNN) to analyze the episode descriptors associated with each patient episode. An example RNN may comprise one or more layers of interconnected nodes, where each node may produce one or more output vectors based on one or more input vectors. In this example, the computing entity may provide episode descriptors as input vectors to the input layer of an example RNN, and nodes in the input layer may produce one or more output vectors, which may be fed into the next layer of nodes. Unlike a typical neural network, an RNN does not limit the size of input vectors and may consider historical information as data traversing through layers of nodes. In some embodiments, an example RNN may output a suggested HHRG code under PDGM for an episode, and the computing entity may establish a data connection between the episode and the corresponding HHRG code under PDGM.

Additionally, or alternatively, the computing entity may implement other machine learning algorithms to determine the corresponding HHRG code for each patient episode. For example, the computing entity may implement one or more of decision tree algorithms, naive Bayes algorithms, support vector machine algorithms, and/or the like.

At step/operation 705, a computing entity (such as the clinical resource computing entity 105 described above in connection with FIG. 1 and FIG. 2) may include means (such as the processing element 205 of the clinical resource computing entity 105 described above in connection with FIG. 2) for calculating model service value points for the plurality of HHRG codes under the PDGM based on the patient episode data.

In some embodiments, after the corresponding HHRG code under PDGM is determined for each patient episode, the computing entity may analyze the distribution pattern data for each HHRG code under PDGM, determine one or more model visit numbers, and calculate the model service value point based on the model visit numbers, similar to those described in connection with method 600 as illustrated in FIG. 6.

In some embodiments, an example computing entity (such as the clinical resource computing entity 105 described above in connection with FIG. 1 and FIG. 2) may update the model service value point for the HHRG code based on actual visit numbers associated with one or more patients having the same HHRG code.

For example, the example computing entity may analyze the distribution pattern of the actual visit numbers for various types of visits and determine one or more updated model visit numbers, similar to those described above in connection with step/operation 604 of FIG. 6. Based on the updated model visit numbers, the computing entity may calculate a new model service value point, similar to those described above in connection with step/operation 606 of FIG. 6.

In some embodiments, an example clinical resource management platform/system may update the model service value points every 24 hours. In some embodiments, an example clinical resource management platform/system may update the model service value points dynamically and at varying time intervals based on the actual visit number. For example, the higher the actual visit number, the more frequently that the clinical resource management platform/system may update the model service value points to reflect the current and most up-to-date information.

C. Exemplary Portfolio Management

Figure 8:
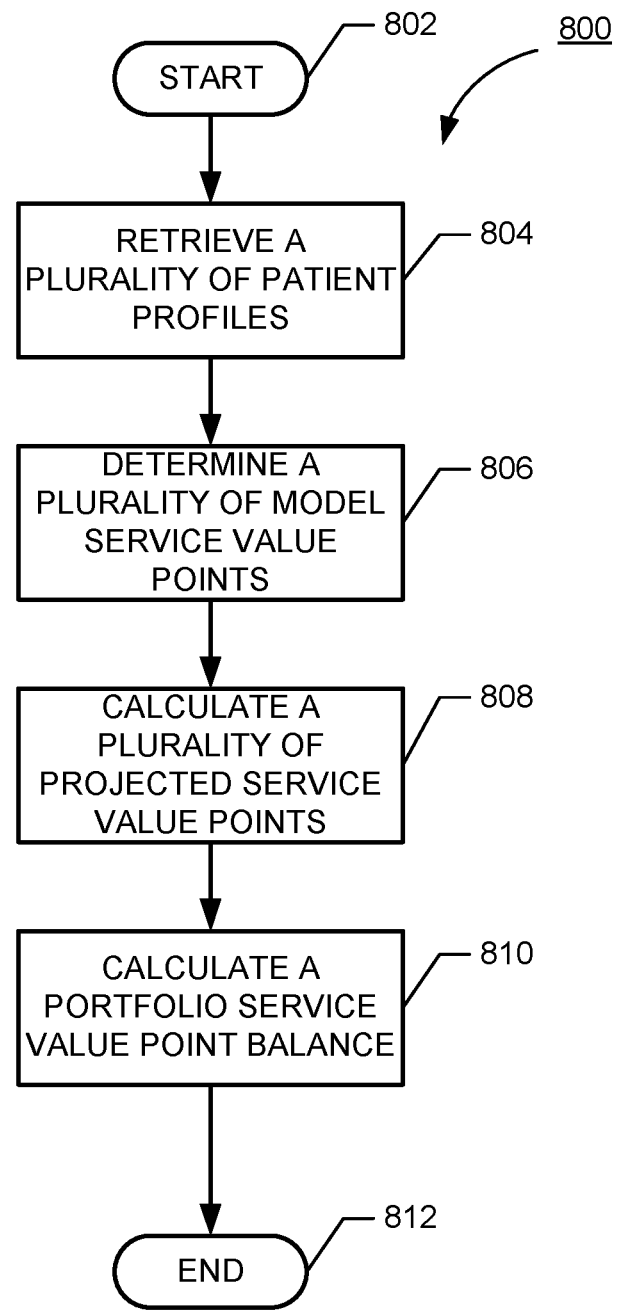

Referring now to FIG. 8, an example method 800 illustrates operation of managing a portfolio of patient profiles in accordance with embodiments of the present disclosure.

The method 800 may start at step/operation 802.

At step/operation 804, a computing entity (such as the clinical resource computing entity 105 described above in connection with FIG. 1 and FIG. 2) may include means (such as the processing element 205 of the clinical resource computing entity 105 described above in connection with FIG. 2) for retrieving a plurality of patient profiles associated with the home healthcare provider.

In some embodiments, each patient profile may comprise a home healthcare provider identifier, which may uniquely identify a home healthcare provider. In some embodiments, the computing entity may transmit a retrieval query to one or more patient profile database based on a home healthcare provider identifier, and may receive one or more patient profiles associated with the home healthcare provider.

At step/operation 806, a computing entity (such as the clinical resource computing entity 105 described above in connection with FIG. 1 and FIG. 2) may include means (such as the processing element 205 of the clinical resource computing entity 105 described above in connection with FIG. 2) for determining a plurality of model service value points for the plurality of patient profiles.

In some embodiments, the computing entity may determine a model service value point for each of the plurality of patient profiles similar to those described in connection with step/operation 404 of FIG. 4, step/operation 503 of FIG. 5, method 600 of FIG. 6, and/or method 700 of FIG. 7.

At step/operation 808, a computing entity (such as the clinical resource computing entity 105 described above in connection with FIG. 1 and FIG. 2) may include means (such as the processing element 205 of the clinical resource computing entity 105 described above in connection with FIG. 2) for calculating a plurality of projected service value points based on a plurality of projected visit numbers for the plurality of patient profiles and the one or more weight values.

In some embodiments, the computing entity may determine a projected service value point for each of the plurality of patient profiles, similar to those described in connection with step/operation 410 of FIG. 4 and/or step/operation 507/509 of FIG. 5.

At step/operation 810, a computing entity (such as the clinical resource computing entity 105 described above in connection with FIG. 1 and FIG. 2) may include means (such as the processing element 205 of the clinical resource computing entity 105 described above in connection with FIG. 2) for calculating a portfolio service value point balance based at least in part on the plurality of model service value points and the plurality of projected service value points.

In some embodiments, the computing entity may calculate a service value point balance for each patient profile based on, for example, subtracting the project service value point from the model service value point for each patient profile, similar to those described above in connection with step/operation 412 of FIG. 4. In some embodiments, the computing entity may calculate the portfolio service value point balance based on adding all service value points balances from all patient profiles associated with a particular home healthcare provider.

In some embodiments, the portfolio service value point balance may indicate the amount of resource that is available for the home healthcare provider. For example, when the portfolio service value point balance is positive, it may indicate that the home healthcare provider may have a surplus of resources for providing healthcare services to the patient. When the portfolio service value point balance is negative, it may indicate that the home healthcare provider may face a shortage of resources for providing healthcare services to the patient.

The method 800 may end at step/operation 812.

In some embodiments, a computing entity (such as the clinical resource computing entity 105 described above in connection with FIG. 1 and FIG. 2) may include means (such as the processing element 205 of the clinical resource computing entity 105 described above in connection with FIG. 2) for causing a display of a clinical resource management interface. Similar to those described above in connection with step/operation 414 of FIG. 4, the clinical resource management interface may be rendered on a display of a clinical resource computing entity (such as the clinical resource computing entity 105 described above in connection with FIG. 1 and FIG. 2), and/or on a display of a user computing entity (such as the user computing entities 101A-101N described above in connection with FIG. 1 and FIG. 3).

Figure 12:
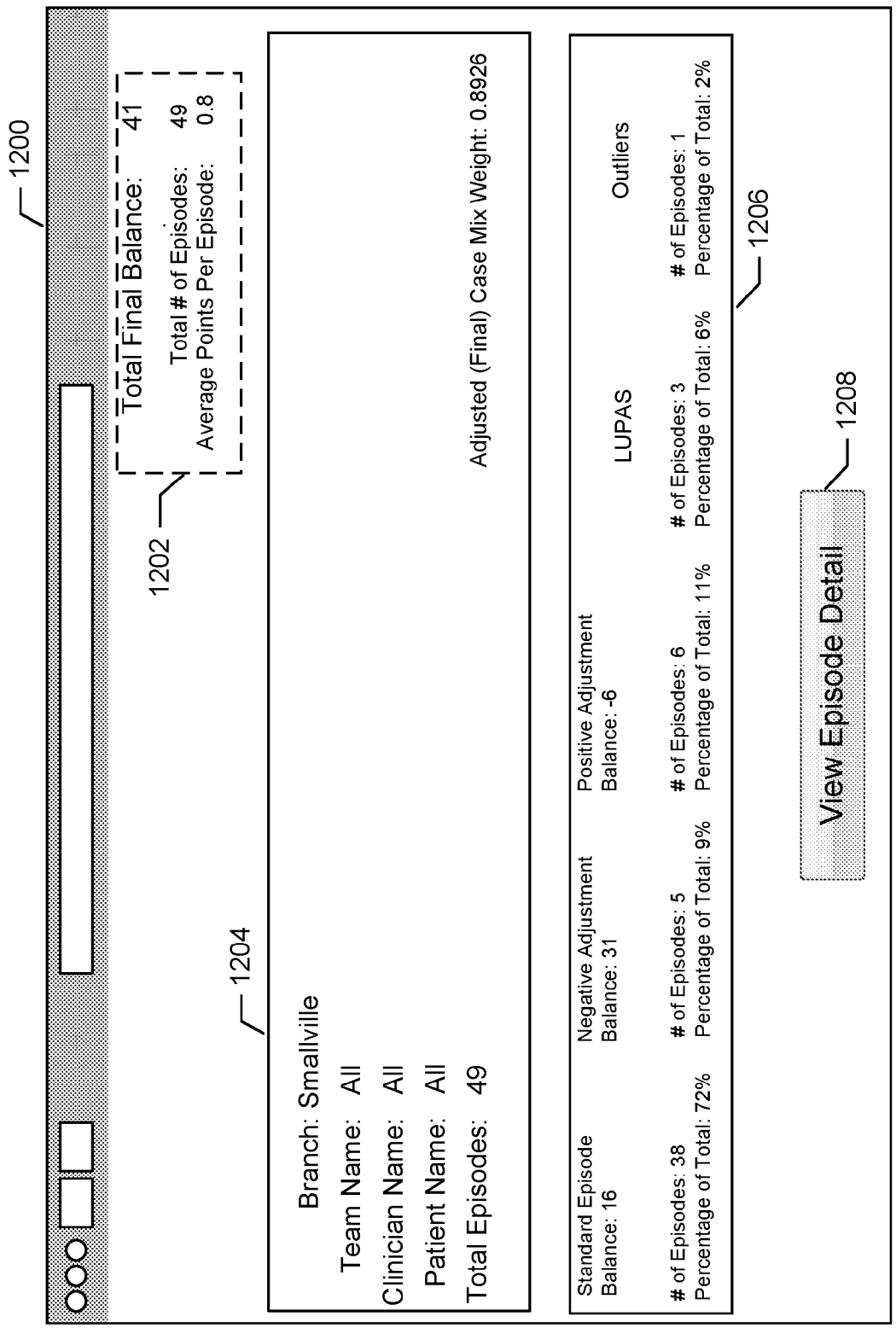
Figure 14:
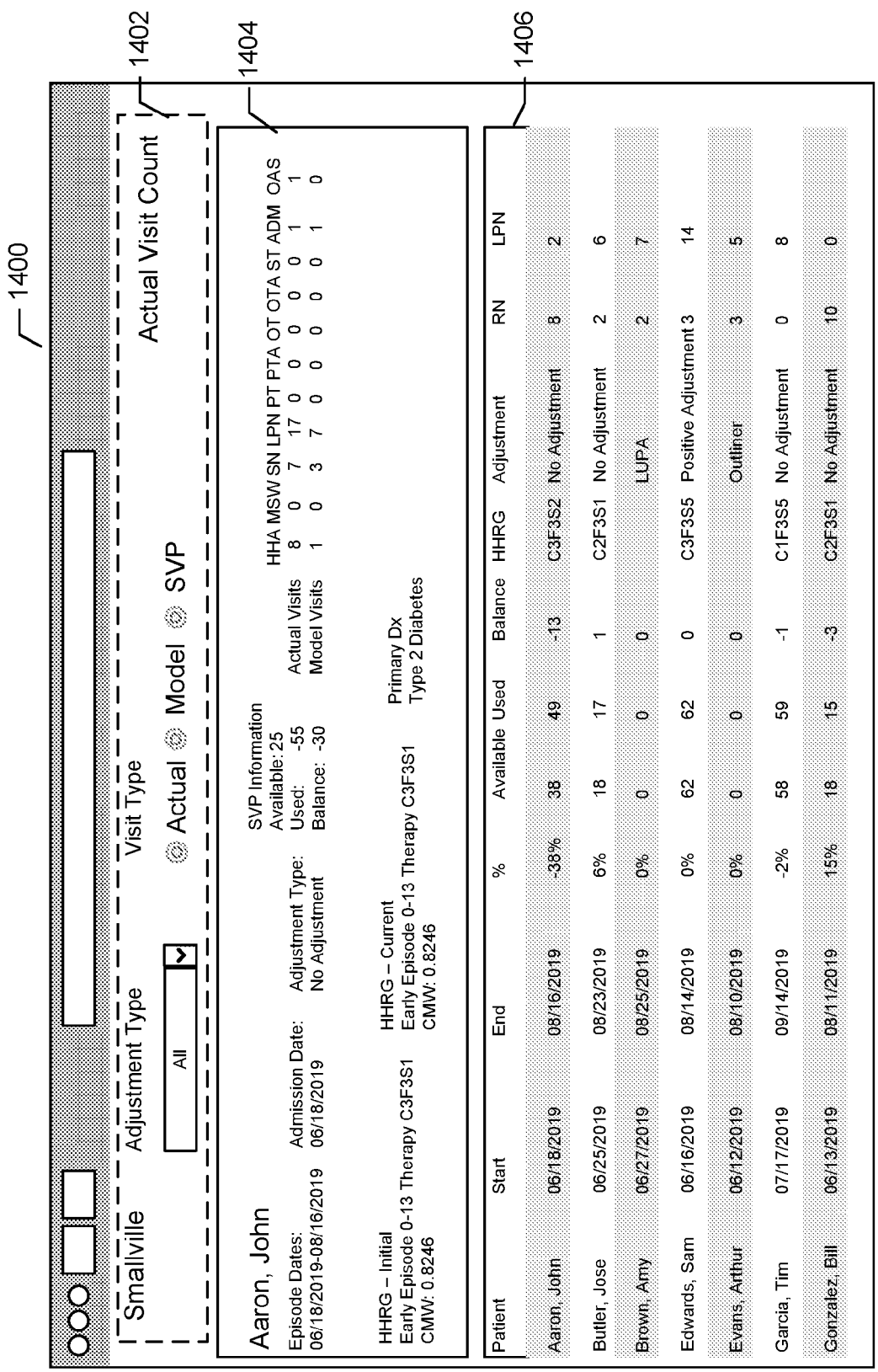

Referring now to FIG. 12, FIG. 13, and FIG. 14, example user interfaces are illustrated.

FIG. 12 illustrates an example user interface 1200 that may facilitate portfolio management.

The example user interface 1200 may comprise a balance summary section 1202, which may provide a portfolio service value point balance that may be calculated based on, for example, method 800 described above in connection with FIG. 8. In the example shown in FIG. 12, the portfolio service value point balance may be 41, the total number of episodes associated with this home healthcare provider may be 49, and an average service value point may be 0.8.

The example user interface 1200 may comprise an information section 1204, which may provide information associated with the home healthcare provider. In the example shown in FIG. 12, the information section 1204 may provide that the home healthcare provider is at Smallville, and may indicate that all terms, all clinicians (i.e. healthcare professionals) and all patients are considered in calculating the portfolio service value point balance. The information section 1204 may also show the adjusted case mix weight for episodes associated with this home healthcare provider.

The example user interface 1200 may comprise an adjustment summary section 1206, which may provide information on adjustments associated with episodes of the home healthcare provider. In the example shown in FIG. 12, the adjustment summary section 1206 may indicate that the standard episode balance is 16, the negative adjustment balance is 31, and the positive adjustment balance is -6. The adjustment summary section 1206 may indicate that the 38 episodes (72% of total episodes) are standard, 5 episodes (9% of total episodes) have a negative adjustment, and 6 episodes (11% of total episodes) have a positive adjustment. The adjustment summary section 1206 may indicate that the 3 episodes (6% of total episodes) have low utilization payment adjustments (LUPAS), and 1 episode (6% of total episodes) is considered as an outlier.

The example user interface 1200 may comprise a "view episode detail" button 1208. When the button 1208 is clicked, tapped, or selected, an example computing entity (such as the clinical resource computing entity 105 described above in connection with FIG. 1 and FIG. 2) may cause rendering of another user interface, such as the user interface 1300 as shown in FIG. 13.

Referring now to FIG. 13, the user interface 1300 may comprise an overview section 1301. In some embodiments, the overview section 1301 may provide the name of the home healthcare provider. The overview section 1301 may provide one or more options that allows a user to filter episodes associated with the home healthcare provider. For example, the overview section 1301 may include a drop-down menu that allows a user to filter the episodes based on the adjustment type. As another example, the overview section 1301 may include one or more radio buttons that allow a user to filter the episodes based on actual visit, model visit, and service value point value. The overview section 1301 may provide an actual visit count.

In some embodiments, the user interface 1300 may comprise an episode listing section 1303, which may provide a listing of episodes associated with the home healthcare provider. The listing may be in tabular format with each row representing a particular patient episode, and each column representing a particular parameter of the corresponding patient episode, such as the patient name, the starting/ending date of the episode, the model service value point ("available"), the projected service value point ("used"), the service value point balance ("balance"), the HHRG code, the adjustment, the actual/projected visit number for each type of visit, and the like. When an episode in the episode listing section 1303 is selected, an example computing entity (such as the clinical resource computing entity 105 described above in connection with FIG. 1 and FIG. 2) may cause rendering of another user interface, such as the user interface 1400 as shown in FIG. 14.

Referring now to FIG. 14, the user interface 1400 may comprise an overview section 1402, which maybe similar to the overview section 1301 described above in connection with FIG. 13. The user interface 1400 may comprise an episode listing section 1406, which maybe similar to the episode listing section 1303 described above in connection with FIG. 13.

The user interface 1400 may comprise a snapshot section 1404, which may provide information associated with the episode that is selected in the episode listing section 1406. For example, the snapshot section 1404 may provide information such as the name of the patient, the starting/ending date of the episode, the admission date, the adjustment type, the model service value point, the projected service value point, the service value point balance, the actual/model visit numbers associated with different types of visits, the HHRG code, and/or the like.

D. Exemplary Alert Generation

Figure 9:
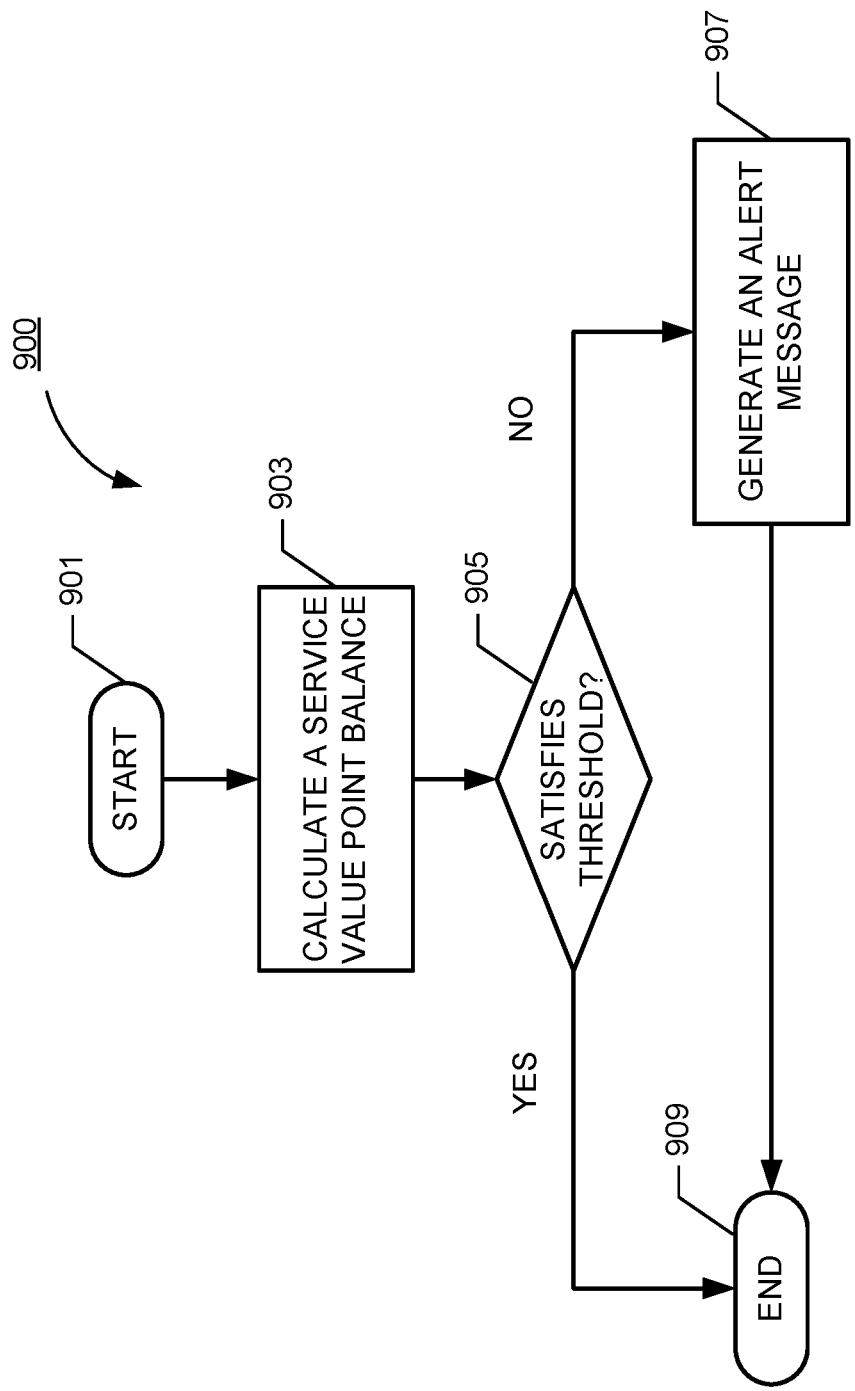

Referring now to FIG. 9, an example method 900 illustrates operation of an example clinical resource management platform/system in accordance with embodiments of the present disclosure.

The example method 900 may start at step/operation 901.

At step/operation 903, a computing entity (such as the clinical resource computing entity 105 described above in connection with FIG. 1 and FIG. 2) may include means (such as the processing element 205 of the clinical resource computing entity 105 described above in connection with FIG. 2) for calculating a service value point balance associated with an episode or an aggregated service value point balance associated with the episode.

For example, the computing entity may calculate the service value point balance (or the aggregated service value point balance) based at least in part on a model service value point and a projected service value point, similar to those described above in connection with step/operation 412 of FIG. 4 and/or step/operation 511 of FIG. 5.

At step/operation 905, a computing entity (such as the clinical resource computing entity 105 described above in connection with FIG. 1 and FIG. 2) may include means (such as the processing element 205 of the clinical resource computing entity 105 described above in connection with FIG. 2) for determining whether the service value point balance (or the aggregated service value point balance) satisfies a service value point threshold.

In some embodiments, the service value point threshold may be determined based on the amount of resource associated with a home healthcare provider. For example, the computing entity may determine a lower service value point threshold for a home healthcare provider with limited resource, as compared to the service value point threshold for a home healthcare provider with more resource. In some embodiments, the service value point threshold may be provided to the computing entity by a user (such as an administrator for the home healthcare provider) operating a user computing entity (for example, user computing entities 101A-101N described above in connection with FIG. 1 and FIG. 3).

In some embodiments, when the service value point balance equals to or is higher than the service value point threshold, the computing entity may determine that the service value point balance satisfies the service value point threshold. For example, if the service value point balance is 11.5 and the service value point threshold is 10, the computing entity may determine that the service value point balance satisfies the service value point threshold.

In some embodiments, when the service value point balance is lower than the service value point threshold, the computing entity may determine that the service value point balance does not satisfy a service value point threshold. For example, if the service value point balance is 9.5 and the service value point threshold is 10, the computing entity may determine that the service value point balance does not satisfy the service value point threshold.

If, at step/operation 905, the computing entity determines that the service value point balance (or the aggregated service value point balance) satisfies the service value point threshold, the method 900 may end at step/operation 909.

If, at step/operation 905, the computing entity determines that the service value point balance (or the aggregated service value point balance) does not satisfy the service value point threshold, the method 900 may proceed to step/operation 907.

At step/operation 907, a computing entity (such as the clinical resource computing entity 105 described above in connection with FIG. 1 and FIG. 2) may include means (such as the processing element 205 of the clinical resource computing entity 105 described above in connection with FIG. 2) for generating an alert message in response to determining that the service value point balance does not satisfy the service value point threshold.

For example, the computing entity may generate an alert message on a user interface (such as the user interface 1000 shown in FIG. 10, the user interface 1100 shown in FIG. 11, the user interface 1200 shown in FIG. 12, the user interface 1300 shown in FIG. 13, and/or the user interface 1400 shown in FIG. 14). The alert message may prompt a user (such as an administrator of the home healthcare provider) to investigate the episode with service value point balance that does not satisfy the service value point threshold.

As described above, the service value point balance may indicate a corresponding remaining resource amount based on what the healthcare provider has allocated to the patient for a given episode and what the patient has already consumed during the episode. In some embodiments, the service value point threshold may indicate a minimum resource amount associated with the home healthcare provider for a patient at a given time point during an episode. When the service value point balance does not satisfy the service value point threshold, it may indicate that the remaining allocated resource for the patient is less than the minimum required amount. In other words, the remaining allocated resource may not be sufficient to support care for the patient. An administrator of the home healthcare provider may, for example, evaluate the patient condition, and determine whether to allocate more resource for healthcare services to the patient.

The example method 900 may end at step/operation 909.

V. Conclusion

Many modifications and other embodiments of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus for programmatically rendering a clinical resource management user interface, the apparatus comprising at least one processor and at least one non-transitory memory comprising program code, the at least one non-transitory memory and the program code configured to, with the at least one processor, cause the apparatus to at least:
generate a first model service value point and a second model service value point for a patient profile, wherein the first model service value point is associated with a first time period and the second model service value point is associated with a second time period;
retrieve one or more weight values associated with one or more types of healthcare professional visits from a home healthcare provider for the patient profile;
generate a first plurality of projected visit numbers associated with the first time period and a second plurality of projected visit numbers associated with the second time period;
generate at least one trained machine learning model based on the patient profile for generating predicted service value points, the patient profile being associated with a patient episode grouping code, the at least one trained machine learning model comprising a deep learning machine learning model trained based at least in part on historical patient episode data associated with the patient episode grouping code;
generate, by the at least one trained machine learning model, a first predicted service value point based at least in part on inputting a first dataset to the at least one trained machine learning model, the first dataset comprising the one or more weight values and the first plurality of projected visit numbers;
generate, by the at least one trained machine learning model, a second predicted service value point based at least in part on inputting a second dataset to the at least one trained machine learning model, the second dataset comprising the one or more weight values and the second plurality of projected visit numbers;
generate an aggregated service value point balance, wherein the at least one non-transitory memory and the program code are configured to, with the at least one processor, cause the apparatus to:
generate a first service value point balance based at least in part on subtracting the first predicted service value point from the first model service value point,
generate a second service value point balance based at least in part on subtracting the second predicted service value point from the second model service value point, and
generate the aggregated service value point balance based at least in part on adding the first service value point balance and the second service value point balance; and
cause rendering the clinical resource management user interface, wherein the clinical resource management user interface comprises a first summary section based at least in part on the first service value point balance and a second summary section based at least in part on the second service value point balance.

2. The apparatus of claim 1, wherein the clinical resource management user interface comprises a first window portion and a second window portion, wherein the first window portion indicates the first model service value point and the first predicted service value point, wherein the second window portion indicates the second model service value point and the second predicted service value point.

3. The apparatus of claim 1, wherein, when generating the first model service value point, the at least one non-transitory memory and the program code are configured to, with the at least one processor, cause the apparatus to further:
retrieve visit distribution pattern data associated with the home healthcare provider;
generate, based on the visit distribution pattern data, one or more model visit numbers corresponding to the one or more types of healthcare professional visits associated with a first Home Health Resource Groups (HHRG) code corresponding to the first time period; and
generate the first model service value point associated with the first time period based at least in part on the one or more model visit numbers and the one or more weight values.

4. The apparatus of claim 1, wherein, when generating the first model service value point and the second model service value point, the at least one non-transitory memory and the program code are configured to, with the at least one processor, cause the apparatus to further:
retrieve patient episode data corresponding to a plurality of patient episodes associated with the home healthcare provider, wherein the patient episode data comprises episode descriptors associated with the plurality of patient episodes;
generate, based on the episode descriptors, a plurality of Home Health Resource Groups (HHRG) codes corresponding to the plurality of patient episodes under a Patient-Driven Groupings Model (PDGM); and
generate model service value points for the plurality of HHRG codes under the PDGM based on the patient episode data.

5. The apparatus of claim 1, wherein the at least one non-transitory memory and the program code are configured to, with the at least one processor, cause the apparatus to further:
update the first model service value point associated with the first time period based on actual visit numbers associated with one or more patients having a same Home Health Resource Groups (HHRG) code.

6. The apparatus of claim 1, wherein the at least one non-transitory memory and the program code are configured to, with the at least one processor, cause the apparatus to further:
retrieve a plurality of patient episodes associated with the home healthcare provider;
generate a plurality of model service value points for the plurality of patient episodes;
generate a plurality of predicted service value points based on a plurality of projected visit numbers for the plurality of patient episodes and the one or more weight values; and
generate a portfolio service value point balance based at least in part on the plurality of model service value points and the plurality of predicted service value points.

7. The apparatus of claim 1, wherein the at least one non-transitory memory and the program code are configured to, with the at least one processor, cause the apparatus to further:

determine whether the aggregated service value point balance satisfies a service value point threshold; and in response to determining that the aggregated service value point balance does not satisfy the service value point threshold, generate an alert message.

8. The apparatus of claim 1, wherein, when generating the at least one trained machine learning model based on the patient profile, the at least one non-transitory memory and the program code are configured to, with the at least one processor, cause the apparatus to:

generate the at least one trained machine learning model based at least in part on a HHRG code associated with the patient profile.

9. A computer-implemented method for rendering a clinical resource management user interface, comprising:

generating a first model service value point and a second model service value point for a patient profile, wherein the first model service value point is associated with a first time period and the second model service value point is associated with a second time period;

retrieving one or more weight values associated with one or more types of healthcare professional visits from a home healthcare provider for the patient profile;

generating a first plurality of projected visit numbers associated with the first time period and a second plurality of projected visit numbers associated with the second time period;

generating at least one trained machine learning model based on the patient profile for generating predicted service value points, the patient profile being associated with a patient episode grouping code, the at least one trained machine learning model comprising a deep learning machine learning model trained based at least in part on historical patient episode data associated with the patient episode grouping code;

generating, by the at least one trained machine learning model, a first predicted service value point based at least in part on inputting a first dataset to the at least one trained machine learning model, the first dataset comprising the one or more weight values and the first plurality of projected visit numbers;

generating, by the at least one trained machine learning model, a second predicted service value point based at least in part on inputting a second dataset to the at least one trained machine learning model, the second dataset comprising the one or more weight values and the second plurality of projected visit numbers;

generating an aggregated service value point balance, comprising:

generating a first service value point balance based at least in part on subtracting the first predicted service value point from the first model service value point, generating a second service value point balance based at least in part on subtracting the second predicted service value point from the second model service value point, and generating the aggregated service value point balance based at least in part on adding the first service value point balance and the second service value point balance; and causing rendering the clinical resource management user interface, wherein the clinical resource management user interface comprises a first summary section based at least in part on the first service value point balance and a second summary section based at least in part on the second service value point balance.

10. The computer-implemented method of claim 9, wherein the clinical resource management user interface comprises a first window portion and a second window portion, wherein the first window portion indicates the first model service value point and the first predicted service value point, wherein the second window portion indicates the second model service value point and the second predicted service value point.

11. The computer-implemented method of claim 9, wherein generating the first model service value point further comprises:

retrieving visit distribution pattern data associated with the home healthcare provider;

generating, based on the visit distribution pattern data, one or more model visit numbers corresponding to the one or more types of healthcare professional visits associated with a first Home Health Resource Groups (HHRG) code corresponding to the first time period; and generating the first model service value point associated with the first time period based at least in part on the one or more model visit numbers and the one or more weight values.

12. The computer-implemented method of claim 9, wherein generating the first model service value point and the second model service value point further comprises:

retrieving patient episode data corresponding to a plurality of patient episodes associated with the home healthcare provider, wherein the patient episode data comprises episode descriptors associated with the plurality of patient episodes;

generating, based on the episode descriptors, a plurality of Home Health Resource Groups (HHRG) codes corresponding to the plurality of patient episodes under a Patient-Driven Groupings Model (PDGM); and generating model service value points for the plurality of HHRG codes under the PDGM based on the patient episode data.

13. The computer-implemented method of claim 9, further comprising:

updating the first model service value point associated with the first time period based on actual visit numbers associated with one or more patients having a same Home Health Resource Groups (HHRG) code.

14. The computer-implemented method of claim 9, further comprising:

retrieving a plurality of patient episodes associated with the home healthcare provider;

generating a plurality of model service value points for the plurality of patient episodes;

generating a plurality of predicted service value points based on a plurality of projected visit numbers for the plurality of patient episodes and the one or more weight values; and generating a portfolio service value point balance based at least in part on the plurality of model service value points and the plurality of predicted service value points.

15. The computer-implemented method of claim 9, further comprising:

determining whether the aggregated service value point balance satisfies a service value point threshold; and in response to determining that the aggregated service value point balance does not satisfy the service value point threshold, generating an alert message.

16. A computer program product for rendering a clinical resource management user interface, the computer program product comprising at least one non-transitory computer-readable storage medium having computer-readable program code portions stored therein, the computer-readable program code portions comprising an executable portion configured to:

generate a first model service value point and a second model service value point for a patient profile, wherein the first model service value point is associated with a first time period and the second model service value point is associated with a second time period;

retrieve one or more weight values associated with one or more types of healthcare professional visits from a home healthcare provider for the patient profile;

generate a first plurality of projected visit numbers associated with the first time period and a second plurality of projected visit numbers associated with the second time period;

generate at least one trained machine learning model based on the patient profile for generating predicted service value points, the patient profile being associated with a patient episode grouping code, the at least one trained machine learning model comprising a deep learning machine learning model trained based at least in part on historical patient episode data associated with the patient episode grouping code;

generate, by the at least one trained machine learning model, a first predicted service value point based at least in part on inputting a first dataset to the at least one trained machine learning model, the first dataset comprising the one or more weight values and the first plurality of projected visit numbers;

generate, by the at least one trained machine learning model, a second predicted service value point based at least in part on inputting a second dataset to the at least one trained machine learning model, the second dataset comprising the one or more weight values and the second plurality of projected visit numbers;

generate an aggregated service value point balance, wherein the computer-readable program code portions comprise the executable portion configured to:

generate a first service value point balance based at least in part on subtracting the first predicted service value point from the first model service value point, generate a second service value point balance based at least in part on subtracting the second predicted service value point from the second model service value point, and generate the aggregated service value point balance based at least in part on adding the first service value point balance and the second service value point balance; and cause rendering the clinical resource management user interface, wherein the clinical resource management user interface comprises a first summary section based at least in part on the first service value point balance and a second summary section based at least in part on the second service value point balance.

17. The computer program product of claim 16, wherein the clinical resource management user interface comprises a first window portion and a second window portion, wherein the first window portion indicates the first model service value point and the first predicted service value point, wherein the second window portion indicates the second model service value point and the second predicted service value point.

18. The computer program product of claim 16, wherein, when generating the first model service value point, the executable portion is configured to further:

retrieve visit distribution pattern data associated with the home healthcare provider;

generate, based on the visit distribution pattern data, one or more model visit numbers corresponding to the one or more types of healthcare professional visits associated with a first Home Health Resource Groups (HHRG) code corresponding to the first time period; and generate the first model service value point associated with the first time period based at least in part on the one or more model visit numbers and the one or more weight values.

19. The computer program product of claim 16, wherein, when generating the first model service value point and the second model service value point, the executable portion is configured to further:

retrieve patient episode data corresponding to a plurality of patient episodes associated with the home healthcare provider, wherein the patient episode data comprises episode descriptors associated with the plurality of patient episodes;

generate, based on the episode descriptors, a plurality of Home Health Resource Groups (HHRG) codes corresponding to the plurality of patient episodes under a Patient-Driven Groupings Model (PDGM); and generate model service value points for the plurality of HHRG codes under the PDGM based on the patient episode data.

\* \* \* \* \*